(12) United States Patent
Zimmermann et al.

(10) Patent No.: US 11,492,594 B2
(45) Date of Patent: *Nov. 8, 2022

(54) METHOD FOR PRODUCING ENGINEERED HEART MUSCLE (EHM)

(71) Applicant: GEORG-AUGUST-UNIVERSITÄT GÖTTINGEN STIFTUNG ÖFFENTLICHEN RECHTS, UNIVERSITÄTSMEDIZIN, Göttingen (DE)

(72) Inventors: Wolfram-Hubertus Zimmermann, Göttingen (DE); Malte Tiburcy, Göttingen (DE); James Hudson, Carina Heights (AU)

(73) Assignee: GEORG-AUGUST-UNIVERSITÄT GÖTTINGEN STIFTUNG ÖFFENTLICHEN RECHTS, UNIVERSITÄTSMEDIZIN, Göttingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/814,186

(22) Filed: Mar. 10, 2020

(65) Prior Publication Data

US 2020/0231934 A1 Jul. 23, 2020

Related U.S. Application Data

(62) Division of application No. 14/913,263, filed as application No. PCT/EP2014/067886 on Aug. 22, 2014, now Pat. No. 10,626,374.

(30) Foreign Application Priority Data

Aug. 22, 2013 (EP) ..................................... 13181352

(51) Int. Cl.
*C12N 5/077* (2010.01)
*C12N 5/00* (2006.01)

(52) U.S. Cl.
CPC ......... *C12N 5/0657* (2013.01); *C12N 5/0037* (2013.01); *C12N 5/0062* (2013.01); *C12N 2500/24* (2013.01); *C12N 2500/30* (2013.01); *C12N 2500/32* (2013.01); *C12N 2500/34* (2013.01); *C12N 2500/36* (2013.01); *C12N 2500/38* (2013.01); *C12N 2500/46* (2013.01); *C12N 2500/90* (2013.01); *C12N 2501/105* (2013.01); *C12N 2501/15* (2013.01); *C12N 2533/54* (2013.01)

(58) Field of Classification Search
CPC .......... C12N 1/00; C12N 5/00; C12N 5/0037; C12N 5/0657; C12N 2500/24; C12N 2500/30; C12N 2500/32; C12N 2500/34; C12N 2500/36; C12N 2500/38; C12N 2500/46; C12N 2500/90; C12N 2501/105; C12N 2501/15; C12N 2533/54
See application file for complete search history.

(56) References Cited

U.S. PATENT DOCUMENTS

| 8,153,427 B2 | 4/2012 | Nistor |
| 10,626,374 B2 * | 4/2020 | Zimmermann ...... C12N 5/0037 |
| 2003/0091979 A1 | 5/2003 | Eschenhagen |
| 2004/0014209 A1 | 1/2004 | Lassar et al. |
| 2009/0061410 A1 | 3/2009 | Zimmermann et al. |
| 2009/0155831 A1 | 6/2009 | Nistor |
| 2010/0167373 A1 | 7/2010 | Zimmermann et al. |
| 2010/0247493 A1 | 9/2010 | Rust et al. |
| 2012/0244619 A1 | 9/2012 | Nakatsuji et al. |
| 2013/0177535 A1 | 7/2013 | Cashman et al. |
| 2013/0189785 A1 | 7/2013 | Palecek et al. |
| 2015/0017718 A1 | 1/2015 | Nakatsuji et al. |
| 2019/0330596 A1 | 10/2019 | Kaneko et al. |

FOREIGN PATENT DOCUMENTS

| AU | 2017239526 A1 | 10/2017 |
| EP | 2840132 A1 | 2/2015 |
| EP | 2842581 A1 | 3/2015 |
| JP | 2006-506047 A | 2/2006 |
| JP | 2011-512855 A | 4/2011 |
| WO | WO 01/55297 A2 | 8/2001 |
| WO | WO 2007/054286 A1 | 5/2007 |
| WO | WO 2008/058917 A1 | 5/2008 |
| WO | WO 2009/007852 A2 | 1/2009 |
| WO | WO 2009/036982 A1 | 3/2009 |
| WO | WO 2010/011352 A2 | 1/2010 |
| WO | WO 2010/144678 A2 | 12/2010 |
| WO | WO 2013/013206 A1 | 1/2013 |
| WO | WO 2013/056072 A1 | 4/2013 |
| WO | WO 2013/063305 A2 | 5/2013 |
| WO | WO 2013/111875 A1 | 8/2013 |
| WO | WO 2017/221975 A1 | 12/2017 |

OTHER PUBLICATIONS

"Smooth muscle cells", Wikipedia page, https://en.wikipedia.org/wiki/Smooth_muscle (Year: 2020).*
"Myocyte", Wikipedia page, https://en.wikipedia.org/wiki/Myocyte (Year: 2020).*
"Iscove's Modification of DMEM Formulation", Corning cellgro, 2012, p. 1.
"TeSRTM1-Published Formulation", StemCell Technologies Technoliges Inc., vol. 24, No. 2, 2006, 1 page.
"Calcium in Cell Culture", https://www.sigmaaldrich.com/life-science/cell-culture/learning-center/media-expert/calcium.html (Year: 2019).
Bird et al. "The human adult cardiomyocyte phenotype", Cardiovascular Research, 58, (2003), pp. 423-434.

(Continued)

*Primary Examiner* — Ruth A Davis
(74) *Attorney, Agent, or Firm* — Birch, Stewart, Kolasch & Birch, LLP

(57) ABSTRACT

The present invention provides a new method for producing Engineered Heart Muscle (EHM) under chemically fully defined conditions all compatible with GMP regulations. The resulting human myocardium generates force and shows typical heart muscle properties.

19 Claims, 15 Drawing Sheets

(56) References Cited

OTHER PUBLICATIONS

Brewer et al., "Neurobasal™ Medium/B27 Supplement: A New Serum-Free Medium Combination for Survival of Neurons," Focus, vol. 16, No. 1, 2014, pp. 6-9.
Brewer et al., "Optimized Survival of Hippocampal Neurons in B27-Supplemented Neurobasal™, a New Serum-free Medium Combination," Journal of Neuroscience Research, vol. 35, 1993, pp. 567-576.
Brown et al. "Analysis of Oxygen Transport in a Diffusion-Limited Model of Engineered Heart Tissue", Biotechnology and Bioengineering, vol. 97, No. 4, pp. 962-975, Jul. 1, 2007.
Burridge et al., "Production of De Novo Cardiomyocytes: Human Pluripotent Stem Cell Differentiation and Direct Reprogramming", Cell Stem Cell, vol. 10, Jan. 6, 2012, pp. 16-28.
Campos et al. "Chromosomal Spread Preparation of Human Embryonic Stem Cells for Karyotyping", Journal of Visualized Experiments 4, (2009).
Cao et al. "Ascorbic acid enhances the cardiac differentiation of induced pluripotent stem cells through promoting the proliferation of cardiac progenitor cells", Cell Research, (2012), 22:219-236.
Carvajal-Vergara et al. "Patient-specific induced pluripotent stem cell derived models of LEOPARD syndrome", Jun. 10, 2010 465(7299): 808-812.
Chan et al. "Live cell imaging distinguishes bona fide human iPS cells from partially reprogrammed cells", Nature Biotechnology, vol. 27, pp. 1033-1037, Nov. 2009.
Corda et al. "Trophic Effect of Human Pericardial Fluid on Adult Cardiac Myocytes: Differential Role of Fibroblast Growth Factor-2 and Factors Related to Ventricular Hypertrophy", Circulation Research, vol. 81, 1997, pp. 679-687.
Costa et al., "The hESC line Envy expresses high levels of GFP in all differential progeny", Nature Methods, vol. 2, 2005. pp. 1-2.
Decker et al., "Regulation of Adult Cardiocyte Growth: Effects of Active and Passive Mechanical Loading", Am. J. Physiol., 272 (Heart Circ. Physiol., 41) (1997) pp. H2902-H2918.
Didié et al., "Parthenogenetic stem cells for tissue-engineered heart repair", The Journal of Clinical Investigation, 2013, pp. 1-14.
Dierickx et al. "Embryonic Template-Based Generation and Purification of Pluripotent Stem Cell-Derived Cardiomyocytes for Heart Repair", J. of Cardiovasc. Trans. Res., (2012), vol. 5, No. 5, pp. 566-580.
Dubois et al., "SIRPA is a specific cell-surfce marker for isolating cardiomyocytes derived from human pluripotent stem cells", Nature Biotechnology, vol. 29, No. 11, 2011, pp. 1011-1018.
Ellerström et al. "Facilitated Expansion of Human Embryonic Stem Cells by Single-Cell Enzymatic Dissociation", Stem Cells 25, pp. 1690-1696, (2007).
English translation of Schneiderbanger, "Zur Bedeutung von Tranforming Growth Factor β1 und Interkleukin-1β für die Morphologie, die Genexpression und die kontraktile Funktion von rekonstituiertem dreidimensi9onalen künstlichen Herzmuskelgewebe," Universitat Hamburg, Dissertation, 2006, p. 113.
English translation of Zimmermann, "Kardiale Regeneration mit künstlichem Herzgewebe," Universitätsklinikum Hamburg Eppendorf, Habilitation, 2006, p. 25.
Eschenhagen et al. "Physiological aspects of cardiac tissue engineering", Am J Physiol Heart Circ Physiol 303, H133-H143, 2012.
Eschenhagen et al., "Engineering Myocardial Tissue", Circulation Research, vol. 97, 2005, pp. 1220-1231.
Eschenhagen et al., "Three-dimensional reconstitution of embryonic cardiomyocytes in a collagen matrix: a new heart muscle model system", The FASEB Journal, vol. 11, 1997, pp. 683-694.
European Search Report for EP 13 18 1352, dated Oct. 31, 2013.
Extended European Search Report for European Application No. 19183577.6, dated Sep. 26, 2019.
Freberg et al. "Epigenetic Reprogramming of OCT4 and NANOG Regulatory Regions by Embryonal Carcinoma Cell Extract", Molecular Biology of the Cell, vol. 18, pp. 1543-1553, May 2007.

Geuss et al., "Making Cardiomyocytes: How Mechanical Stimulation Can Infulence Differentiation of Pluripotent Stem Cells", Biotechnol. Prog., vol. 29, No. 5 (2013) pp. 1089-1096.
Goumans et al., "TGF-β1 Induces Efficient Differentiation of Human Cardiomyocyte Progenitor Cells into Functional Cardiomyocytes in vitro", Stem Cell Research, vol. 1 (2008) pp. 138-149.
Hanna Lab, "B27 Supplement (AKAB22)," Hanna Lab Protocol, Weizmann Institute of Science, Last updated Feb. 17, 2016, pp. 1-5.
Heng et al., "Strategies for Directing the Differentiation of Stem Cells into the Cardiomyogenic Lineage in vitro", Cardiovascular Research, vol. 62 (2004) pp. 34-42.
Hudson et al. "Development of Myocardial Constructs Using Modulus-Matched Acrylated Polypropylene Glycol Triol Substrate and Different Nonmyocyte Cell Populations", Tissue Engineering: Part A, vol. 17, Nos. 17 and 18, 2011.
Hudson et al. "Tuning Wnt-signaling to enhance cardiomyogenesis in human embryonic and induced pluripotent stem cells", Journal of Molecular and Cellular Cardiology, vol. 51, No. 3, 2011, pp. 277-279.
Hudson et al., "Primitive Cardiac Cells from Human Embryonic Stem Cells", Stem Cells and Development, vol. 21, No. 9, 2012, pp. 1513-1523.
International Search Report issued in PCT/EP2014/067886, dated Oct. 2, 2014.
International Search Report, issued in PCT/EP2014/069951, PCT/ISA/210, dated Dec. 18, 2014.
Irion et al. "Identification and targeting of the ROSA26 locus in human embryonic stem cells", Nature Biotechnology, vol. 25, No. 12, pp. 1477-1482, Dec. 2007.
Itzhaki et al. "Modelling the long QT syndrome with induced pluripotent stem cells", Nature, vol. 471, pp. 225-229, Mar. 10, 2011.
Japanese Office Action issued in corresponding Japanese Patent Application No. 2016-515530 dated May 22, 2018.
Japanese Office Action, dated Jul. 17, 2018, for Japanese Application No. 2016-535491, along with an English translation.
Kattman et al., "Stage-Specific Optimization of Activin/Nodal and BMP Signaling Promotes Cardiac Differentiation of Mouse and Human Pluripotent Stem Cell Lines", Cell Stem Cell, vol. 8, Feb. 4, 2011, pp. 228-240.
Kehat et al., "Human embryonic stem cells can differentiate into myocytes with structural and functional properties of cardiomyocytes", The Journal of Clinical Investigation, vol. 108, No. 3, Aug. 2001, pp. 407-414.
Kensah et al., "Murine and human pluripotent stem cell-derived cardiac bodies form contractile myocardial tissue in vitro", European Heart Journal, 2012, pp. 1-14.
Kofidis et al., "In vitro engineering of heart muscle: Artificial myocardial tissue", The Journal of Thoracic and Cardiovascular Surgery, vol. 124, No. 1, 2002, pp. 63-69.
Kruithof et al. "TGFβ and BMP signaling in cardiac cushion formation: Lessons from mice and chicken", Differentiation, 84, (2012), pp. 89-102.
Lian et al. "Directed cardiomyocyte differentiation from human pluripotent stem cells by modulating Wnt/β-catenin signaling under fully defined conditions", Nature Protocols, vol. 8, No. 1, pp. 162-174, (2013).
Lian et al. "Insulin Inhibits cardiac mesoderm, not mesendoderm, formation during cardiac differentiation of human pluripotent stem cells and modulation of canonical Wnt signaling can rescue this inhibition", Stem Cells, Mar. 2013, 31(3), pp. 447-457.
Lian et al., "Robust cardiomyocyte differentiation from human pluripotent stem cells via temporal modulation of canonical Wnt signaling", PNAS, May 29, 2012, pp. E1848-E1857.
Long et al., "Artefacts in Cell Culture: Pyruvate as a Scavenger of Hydrogen Peroxide Generated by Ascorbate or Epigallocatechin Gallate in Cell Culture Media", Biochemical and Biophysical Research Communications, vol. 388 (2009) pp. 700-704.
Lopaschuk et al., "Energy Metabolic Phenotype of the Cardiomyocyte During Development, Differentiation, and Postnatal Maturation", J Cardiovasc Parmacol, vol. 56, No. 2, Aug. 2010, pp. 130-140.

(56) References Cited

OTHER PUBLICATIONS

Malan et al. "Cardiomyocytes Obtained From Induced Pluripotent Stem Cells With Long-QT Syndrome 3 Recapitulate Typical Disease-Specific Features In Vitro", Circulation Research 109(8), pp. 841-847, (2011).
Mauritz et al. "Generation of Functional Murine Cardiac Myocytes From Induced Pluripotent Stem Cells", Circulation, vol. 118, No. 5, pp. 507-517, (2008).
Molin et al., "Expression Patterns of Tgfbeta1-3 Associate With Myocardialisation of the Outflow Tract and the Development of the Epicardium and the Fibrous Heart Skeleton", Developmental Dynamics, vol. 227, 2003, pp. 431-444.
Moretti et al. "Patient-Specific Induced Pluripotent Stem-Cell Models for Long-QT Syndrome", The New England Journal of Medicine, vol. 363, No. 15, Oct. 7, 2010, pp. 1397-1409.
Morritt et al., "Cardiac Tissue Engineering in an In Vivo Vascularized Chamber", Circulation, vol. 115, 2007, pp. 353-360.
Mummery et al., "Differentiation of Human Embryonic Stem Cells and Induced Pluripotent Stem Cells to Cardiomyocytes", Circulation Research, vol. 111, Jul. 20, 2012, pp. 344-358.
Mummery et al., "Differentiation of Human Embryonic Stem Cells to Cardiomyocytes: Role of Coculture With Visceral Endoderm-Like Cells", Circulation, vol. 107, 2002, pp. 2733-2740.
Naito et al., "Optimizing Engineered Heart Tissue for Therapeutic Applications as Surrogate Heart Muscle", Circulation, vol. 114, 2006, pp. I-72-I-78.
Neagoe et al. "Titin Isoform Switch in Ischemic Human Heart Disease", Circulation 106, pp. 1333-1341, (2002).
Odiete et al., "Neuregulin in Cardiovascular Development and Disease", Circ. Res., vol. 111, No. 10, Oct. 26, 2012, pp. 1376-1385.
Pakzad et al., "Presence of a ROCK Inhibitor in Extracellular Matrix Supports More Undifferentiated Growth of Feeder-Free Human Embryonic and Induced Pluripotent Stem Cells upon Passaging", Stem Cell Rec and Rep, vol. 6 (2010) pp. 96-107.
Park et al. "Reprogramming of human somatic cells to pluripotency with defined factors", Nature, vol. 451, pp. 141-146, Jan. 10, 2008.
Passier et al., "increased Cardiomyocyte Differentiation from Human Embryonic Stem Cells in Serum-Free Cultures", Stem Cells, vol. 23, 2005, pp. 772-780.
Price et al., "Effects of Platelet-Derived Growth Factor-AA and -BB on Embryonic Cardiac Development", The Anatomical Record Part A, vol. 272A, 2003, pp. 424-433.
Radisic et al, "Functional assembly of engineered myocardium by electrical stimulation of cardiac myocytes cultured on scaffolds", PNAS, vol. 101, No. 52, Dec. 28, 2004, pp. 18129-18134.
Schaaf et al., "Human Engineered Heart Tissue as a Versatile Tool in Basic Research and Preclinical Toxicology", PLoS One, vol. 6, Issue 10, Oct. 2011, pp. 1-11.
Schroeder et al., "Differentiation and Lineage Selection of Mouse Embryonic Stem Cells in a Stirred Bench Scale Bioreactor with Automated Process Control", Biotechnology and Bioengineering, vol. 92, No. 7, Dec. 30, 2005, pp. 920-933.
Shimizu et al., "Fabrication of Pulsatile Cardiac Tissue Grafts Using a Novel 3-Dimenstional Cell Sheet Manipulation Technique and Temperature-Responsive Cell Culture Surfaces", Circulation Research, vol. 90, 2002, pp. e40-e48.
Shimko et al., "Effect of Mechanical Loading on Three-Dimensional Cultures of Embryonic Stem Cell-Derived Cardiomyocytes", Tissue Engineering: Part A, vol. 14, No. 1 (2008) pp. 49-58.
Shimojo et al., "Contributory role of VEGF overexpression in endothelin-1-induced cardiomyocyte hypertrophy", Am J Physiol Heart Circ Physiol, vol. 293, 2007, pp. H474-H481.
Sigma-Aldrich, "Material constituting the cell enviroment and culture medium," URL:https://www.sigmaaldrich.com/content/dam/sigma-aldrich/docs/SAJ/Brochure/1/j_recipeccmediumbasic.pdf, sigma-aldrich.com, Jul. 2013, 6 pages.
Soong et al. "Development of a novel technology to engineer heart muscle for contractile and paracrine support in heart failure", Internet Citation, 2012.
Soong et al., "Cardiac Differentiation of Human Embryonic Stem Cells and their Assembly into Engineered Heart Muscle", Current Protocols in Cell Biology, vol. 55, 2012, pp. 23.8.1-23.8.21.
Streckfuss-Bomeke et al., "Comparative study of human-induced pluripotent stem cells derived from bone marrow cells, hair keratinocytes, and skin fibroblasts", European Heart Journal, vol. 34, 2013, pp. 2618-2629.
Takahashi et al. "Induction of Pluripotent Stem Cells from Adult Human Fibroblasts by Defined Factors", Cell 131, pp. 861-872, Nov. 30, 2007.
Takahashi et al., "induction of Pluripotent Stem Cells from Mouse Embryonic and Adult Fibroblast Cultures by Defined Factors", Cell, vol. 126, Aug. 25, 2006, pp. 663-676.
Thomson et al., "Embryonic Stem Cell Lines Derived from Human Blastocysts", Science, vol. 282, Nov. 6, 1998, pp. 1145-1147.
Tiburcy et al., "Modeling myocardial growth and hypertrophy in engineered heart muscle", Trends in Cardiovascular Medicine, 2013, pp. 7-13.
Tiburcy et al., "Terminal Differentiation, Advanced Organotypic Maturation, and Modeling of Hypertrophic Growth in Engineered Heart Tissue", Circulation Research, vol. 109, Oct. 28, 2011, pp. 1105-1114.
Tulloch et al., "Growth of Engineered Human Myocardium with Mechanical Loading and Vascular Co-culture", Circulation Research, vol. 109, No. 1, Jun. 24, 2011, pp. 47-59.
U.S. Notice of Allowance for U.S. Appl. No. 14/917,103, dated Feb. 28, 2019.
U.S. Notice of Allowance for U.S. Appl. No. 14/917,103, dated Jun. 14, 2018.
U.S. Office Action for U.S. Appl. No. 14/917,103, dated Aug. 31, 2017 (Restriction/Election Requirement).
U.S. Office Action for U.S. Appl. No. 14/917,103, dated Oct. 17, 2018.
U.S. Office Action for U.S. Appl. No. 14/917,103, dated Feb. 9, 2018.
Uosaki et al., "Efficient and Scalable Purification of Cardiomyocytes from Human Embryonic and Induced Pluripotent Stem Cells by VCAM1 Surface Expression", PLOS One, vol. 6m No. 8 (2011) e23657 pp. 1-9.
Vandenburgh et al., "Mechanical Stimulation of Organogenic Cardiomyocyte Growth in vitro", Am. J. Physiol., vol. 270 (Cell Physiol. 39) (1996) pp. C1284-C1292.
Vantler et al., "PDGF-BB protects cardiomyocytes from apoptosis and improves contractile function of engineered heart tissue", Journal of Molecular and Cellular Cardiology, vol. 48, 2010, pp. 1316-1323.
Watanabe et al., "A ROCK Inhibitor Permits Survival of Dissociated Human Embryonic Stem Cells", Nature Biotechnology, vol. 25, No. 6 (2007) pp. 681-686.
Wollert et al., "Cardiotrophin-1 and the role of gp130-dependent signaling pathways in cardiac growth and development", J Mol Med, vol. 75, 1997, pp. 492-501.
Written Opinion of the International Searching Authority issued in PCT/EP2014/067886, dated Oct. 2, 2014.
Written Opinion of the International Searching Authority, issued in PCT/EP2014/069951, PCT/ISA/237, dated Dec. 18, 2014.
Xu et al., "Characterization and Enrichment of Cardiomyocytes Derived From Human Embryonic Stem Cells", Circulation Reseach, vol. 91, 2002, pp. 501-508.
Yang et al., "Human cardiovascular progenitor cells develop from a KDR+ embryonic-stem-cell-derived population", Nature, vol. 453, May 22, 2008, pp. 524-528.
Yazawa et al. "Using iPS cells to investigate cardiac phenotypes in patients with Timothy Syndrome", Nature 471, pp. 230-234, Mar. 10, 2011.
Ye et al., "Patching the Heart Cardiac Repair From Within and Outside," Circulation Research, vol. 113, Sep. 13, 2013, pp. 922-932 (12 pages total).
Zhang et al. "Functional Cardiomyocytes Derived from Human Induced Pluripotent Stem Cells", Circulation Research 104, e30-41, Feb. 27, 2009.
Zimmerman et al., Eur J Immunol 2015 45: 1270-1273, Technical Comment (Year: 2015).

(56) References Cited

OTHER PUBLICATIONS

Zimmermann et al., "Engineered heart tissue grafts improve systolic and diastolic function in infarcted rat hearts", Nature Medicine, vol. 12, No. 4, Apr. 2006, pp. 452-458.

Zimmermann et al., "Heart muscle engineering: An update on cardiac muscle replacement therapy", Cardiovascular Research, vol. 71, 2006, pp. 419-429.

Zimmermann et al., "Three-Dimensional Engineered Heart Tissue from Neonatal Rat Cardiac Myocytes", Biotechnology and Bioengineering, vol. 68, No. 1, Apr. 5, 2000, pp. 106-114.

Zimmermann et al., "Tissue Engineering of a Differentiated Cardiac Muscle Construct", Circulation Research, vol. 90, Feb. 8, 2002, pp. 223-230.

Zimmermann, "Embryonic and embryonic-like stem cells in heart muscle engineering", Journal of Molecular and Cellular Cardiology, vol. 50, 2011, pp. 320-326.

Extended European Search Report for European Application No. 20188364.2, dated Feb. 2, 2021.

Floy et al., "Human pluripotent stem cell-derived cardiac stromal cells and their applications in regenerative medicine," Stem Cell Research, vol. 45, No. 101831, 2020, 14 pages.

Giacomelli et al., "Human-iPSC-Derived Cardiac Stromal Cells Enhance Maturation in 3D Cardiac Microtissues and Reveal Non-cardiomyocyte Contributions to Heart Disease," Cell Stem Cell, vol. 26, Jun. 4, 2020, pp. 862-879 (30 pages total).

Guadix et al., "Human Pluripotent Stem Cell Differentiation into Functional Epicardial Progenitor Cells," Stem Cell Reports, vol. 9, Dec. 12, 2017, pp. 1754-1764.

Schlick, "Fibroblast-Cardiomyocyte Cross-Talk in Heart Muscle Formation and Function," Doctoral Thesis, Georg-August University Göttingen, Nov. 2018, pp. 1-139 (161 pages total).

Tiburcy et al., "Defined Engineered Human Myocardium with Advanced Maturation for Applications in Heart Failure Modelling and Repair," Circulation, vol. 135, No. 19, May 9, 2017, pp. 1832-1847 (27 pages total).

Tran et al., "Efficient Differentiation of Human Pluripotent Stem Cells into Mesenchymal Stem Cells by Modulating Intracellular Signaling Pathways in a Feeder/Serum-Free System," Stem Cells and Development, vol. 21, No. 7, 2012, pp. 1165-1175.

Witty et al., "Generation of the epicardial lineage from human pluripotent stem cells," Nature Biotechnology, vol. 32, No. 10, Oct. 2014, pp. 1026-1035 (12 pages total).

Asnes et al., "Reconstitution of the Frank-Starling Mechanism in Engineered Heart Tissues", Biophysical Journal, vol. 91, Sep. 2006, pp. 1800-1810.

Freshney, R., Culture of Cells for Tissue Engineering, John Wiley & Sons, Inc., 2006, pp. 1-512, 517 pages total.

Gerisch et al., "Qualitative and Quantitative Analysis of Cardiac Progenitor Cells in Cases of Myocarditis and Cardiomyopathy", Frontiers in Genetics, vol. 9, Article 72, Mar. 6, 2018, pp. 1-23.

U.S. Office Action for U.S. Appl. No. 16/138,101, dated Jun. 3, 2021.

Extended European Search Report issued in Application No. 20203316.3 dated Apr. 8, 2021.

Janssen et al., "Myocardial contraction-relaxation coupling," Am J Heart Circ Physiol, vol. 299, Sep. 17, 2010, pp. H1741-H1749.

U.S. Office Action for U.S. Appl. No. 16/138,101, dated Feb. 7, 2022.

Author Unknown, "Extracellular Matrix; (ECM)," Heart's Selection 1, vol. 43, No. 12, 2011, pp. 1492-1495, 5 pages total, with a partial English translation.

English translation of the Japanese Decision of Rejection for Japanese Application No. 2020-052526, dated May 10, 2022.

* cited by examiner

METHOD FOR PRODUCING ENGINEERED HEART MUSCLE (EHM)

CROSS-REFERENCE TO RELATED APPLICATIONS

This application is a Divisional Application Ser. No. 14/913,263, filed on Feb. 19, 2016, which is the National Phase under 35 U.S.C. § 371 of International Application No. PCT/EP2014/067886, filed on Aug. 22, 2014, which claims the benefit under 35 U.S.C. § 119(a) to Patent Application No. 13181352.9, filed in Europe on Aug. 22, 2013, all of which are hereby expressly incorporated by reference into the present application.

The present invention provides a new method for producing Engineered Heart Muscle (EHM) under chemically fully defined conditions all compatible with GMP regulations. The resulting human myocardium generates force and shows typical heart muscle properties.

BACKGROUND OF THE INVENTION

Heart disease is the number one cause of death in industrialized countries and its prevalence is expected to rise despite refined pharmacological and interventional treatment. Consequently, novel pharmacological and non-pharmacological treatment modalities are inevitably called for. Tissue engineered myocardium can on the one hand be used to identify new drugs or drug targets for the treatment of heart disease (substance screening/target validation) and may on the other hand be directly applied in cardiac repair (regenerative/reparative medicine) (Eschenhagen & Zimmermann Circ Res 97: 1220-1231 (2005); Zimmermann et al. Cardiovasc Res 71: 419-429 (2006)). A main prerequisite of functional engineered myocardium, as of native heart muscle, is the ability to generate force.

Several myocardial tissue engineering modalities have been established throughout the past decade. However, reliable force-generation has only been demonstrated using hydrogel-cell-entrapment (Eschenhagen et al. Faseb J 11: 683-694 (1997); Kofidis et al. J Thorac Cardiovasc Surg 124: 63-69 (2002); Morritt et al. Circulation 115: 353-360 (2007); Zimmermann et al. Biotechnol Bioeng 68: 106-114 (2000); Tulloch et al. Circ Res 109: 47-59 2011)) or cell-sheet technologies (Shimizu et al. Circ Res 90: e40 (2002)). The inventors and others have provided evidence that myocyte entrapment in collagen-hydrogels offer a three-dimensional growth milieu that can on the one hand facilitate assembly of multicellular, anisotropic cardiac muscle and on the other hand support advanced maturation of immature cardiomyocytes (Tiburcy et al. Circ Res 109: 1105-1114 (2011)). Resulting engineered heart muscle (EHM) preparations (formerly described as engineered heart tissue: EHT) ultimately facilitate the formation of contractile myocardial constructs with properties of postnatal heart muscle (Radisic et al. Proc Natl Acad Sci USA 101: 18129-18134 (2004); Tiburcy et al. Circ Res 109: 1105-1114 (2011); Zimmermann et al. Circ Res 90: 223-230 (2002)). Proof-of principle animal studies have shown that after implantation onto diseased hearts EHMs not only electrically integrate but also improve heart function (Zimmermann et al. Nat Med 12: 452-458 (2006)).

In principle, the inventors have shown that tissue engineered myocardium may be a novel treatment modality for diseased heart. However, all published cardiac tissue engineering approaches so far rely on the use of undefined animal components, mostly animal matrix (e.g. rat collagen, bovine fibrin, mouse tumor-derived extracellular matrix [Matrigel®]), and animal serum (Tulloch et al. Circ Res 109: 47-59 (2011), Zimmermann et al. Circ Res 90: 223-230 (2002), Zimmermann et al. Nat Med 12: 452-458 (2006), Schaaf et al. PLoS One 6: e26397 (2011); Soong et al. Curr Prot Cell Biol 23.8.1-23.8.21 (2012); WO 01/55297, WO 2007/054286, and WO 2008/058917). In the rat EHM model the inventors have performed first studies to replace animal serum with a serum-free medium. While the inventors were able to achieve a comparable force production in resulting tissues, the inventors could not take out animal components during the initial phase of tissue formation in the first seven days (Naito et al. *Circulation* 114: 172-78 (2006); Zimmermann, Universitätsklinikum Hamburg Eppendorf, Habilitation (2006); Schneiderbanger, Universität Hamburg, Dissertation (2006)).

Recently, several serum-free, cytokine-directed protocols for more efficient cardiac differentiations have been described (Burridge et al. *Cell Stem Cell* 10: 16-28 (2012)) yielding cultures containing up to 98% cardiomyocytes (Lian et al. *Proc Natl Acad Sci USA* (2012)). Importantly, these serum-free differentiation protocols offer potential clinical applicability as defined substances without animal products are utilized. Whilst scaling of human heart cells under GMP conditions appears to be a resolvable caveat, the generation of human force-generating myocardium still remains a challenge. It remains a pivotal issue to support organotypic organization and advanced maturation of ESC-derived myocytes under defined, serum-free culture conditions.

SUMMARY OF THE INVENTION

Here, the inventors report a protocol to engineer human myocardium (Human Engineered Heart Muscle: hEHM) using all defined components. These components include a hydrogel matrix, human cells and serum-free culture medium conditions all compatible with GMP regulations. The resulting human myocardium generates force and shows typical heart muscle properties.

More specifically, a method for producing engineered heart muscle (EHM) is provided, the method comprising the steps of:

i) providing a serum-free reconstitution mixture in one or more moulds, said reconstitution mixture comprising (a) a serum-free minimum essential medium; (b) a serum-free supplement resulting in a final concentration of 0.5-50 mg/ml albumin, 1-100 µg/ml transferrin, 0.1-10 µg/ml ethanol amine, 0.003-0.3 µg/ml sodium selenite, 0.4-40 µg/ml L-Carnitine HCl, 0.1-10 µg/ml Hydrocortisone, 0.05-5 µl/ml Fatty acid supplement, 0.0001-0.1 µg/ml triodo-L-thyronine (T3) and 0.2-2 mg/ml collagen; and (c) a mixture of human cardiac myocytes and human non-myocytes, wherein 20 to 80% of the total cell mixture are cardiac myocytes; wherein the reconstitution mixture has a pH of 7.2 to 7.6;

ii) culturing the serum-free reconstitution mixture in said one or more moulds, whereby the serum-free reconstitution mixture is allowed to condense for at least 15 min;

iii) culturing the mixture obtained in step (ii) in said one or more moulds in a serum-free EHM culture medium until the mixture condenses to at least 50% of its original thickness, wherein said EHM culture medium comprises (a) a basal medium comprising 0.5-3 mmol/L $Ca^{2+}$; (b) a serum-free supplement as defined in (i)(b); (c) 0.5-10 mmol/L L-glutamine; (d) 0.01-1.0 mmol/L ascorbic acid; (e) 1-100 ng/ml IGF-1; and (f) 1-10 ng/ml TGFβ1;

iv) culturing the mixture obtained in step (iii) under mechanical stretching in a serum-free EHM culture medium as defined in step (iii) (a)-(f), whereby force-generating EHM is formed.

DETAILED DESCRIPTION OF THE PREFERRED EMBODIMENTS

More specifically, the invention provides a method for producing engineered heart muscle (EHM), the method comprising the steps of:

(i) providing a serum-free reconstitution mixture in one or more moulds, said reconstitution mixture comprising (a) a serum-free minimum essential medium; (b) a serum-free supplement resulting in a final concentration of 0.5-50 mg/ml albumin (preferably 1-40 mg/ml, more preferably 2-30 mg/ml, still more preferably 3-20 mg/ml, most preferably 4-10 mg/ml, and even most preferably 4.5-7.5 mg/ml such as about 5 mg/ml),
1-100 µg/ml transferrin (preferably 2-90 µg/ml, more preferably 3-80 µg/ml, even more preferably 4-70 µg/ml, still more preferably 5-60 µg/ml, more preferably 6-50 µg/ml, more preferably 7-40 µg/ml, more preferably 8-30 µg/ml, more preferably 9-20 µg/ml, such as about 10 µg/ml),
0.1-10 µg/ml ethanol amine (preferably 0.2-9 µg/ml, more preferably 0.3-8 µg/ml, even more preferably 0.4-7 µg/ml, still more preferably 0.5-6 µg/ml, more preferably 0.6-5 µg/ml, more preferably 0.7-4 µg/ml, more preferably 0.8-3 µg/ml, more preferably 1-2.5 µg/ml, such as about 2 µg/ml),
0.003-0.3 µg/ml sodium selenite (preferably 0.005-0.2 µg/ml, more preferably 0.01-0.1 µg/ml, even more preferably 0.02-0.05 µg/ml, and most preferably about 0.03 µg/ml, such as about 0.032 µg/ml),
0.4-40 µg/ml L-Carnitine HCl (preferably 0.5-30 µg/ml, more preferably 1-20 µg/ml, even more preferably 2-10 µg/ml, most preferably 3-5 µg/ml, and even most preferably about 4 µg/ml),
0.1-10 µg/ml Hydrocortisone (preferably 0.2-9 µg/ml, more preferably 0.3-8 µg/ml, even more preferably 0.4-7 µg/ml, still more preferably 0.5-6 µg/ml, more preferably 0.6-5 µg/ml, more preferably 0.7-4 µg/ml, more preferably 0.8-3 µg/ml, more preferably 0.9-2 µg/ml, such as about 1 µg/ml),
0.05-5 µl/ml Fatty acid supplement (preferably 0.1-4 µl/ml, more preferably 0.2-3 µl/ml, even more preferably 0.3-3 µl/ml, most preferably 0.4-2 µl/ml, and even most preferably 0.45-1 µl/ml, such as about 0.5 µg/ml),
0.0001-0.1 µg/ml triodo-L-thyronine (T3) (preferably 0.001-0.01 µg/ml, more preferably 0.002-0.0075 µg/ml, even more preferably 0.003-0.005 µg/ml, and most preferably about 0.004 µg/ml), and
0.2-2 mg/ml collagen (preferably 0.3-1.9 mg/ml, more preferably 0.4-1.8 mg/ml, even more preferably 0.4-1.7 mg/ml, still more preferably 0.5-1.6 mg/ml, more preferably 0.6-1.5 mg/ml, more preferably 0.7-1.4 mg/ml, more preferably 0.8-1.3 mg/ml, more preferably 0.9-1.2 mg/ml, such as about 1 mg/ml);
and (c) a mixture of human cardiac myocytes and human non-myocytes, wherein 20 to 80% of the total cell mixture are cardiac myocytes;
wherein the reconstitution mixture has a pH of 7.0 to 7.8, preferably 7.1 to 7.7, more preferably 7.2 to 7.6, even more preferably 7.3 to 7.5, and most preferably about 7.4;

(ii) culturing the serum-free reconstitution mixture in said one or more moulds, whereby the serum-free reconstitution mixture is allowed to condense for at least 15 min, preferably 0.25-3 h, and more preferably for 0.5-1.5 h, (iii) culturing the mixture obtained in step (ii) in said one or more moulds in a serum-free EHM culture medium until the mixture condenses to at least 50% (preferably at least 55%, more preferably at least 60%, even more preferably at least 70%, and most preferably at least 75%) of its original thickness,
wherein said EHM culture medium comprises
(a) a basal medium comprising 0.5-3 mmol/L $Ca^{2+}$ (preferably 1-2.5 mmol/L, more preferably about 2 mmol/L);
(b) a serum-free supplement as defined in (i)(b);
(c) 0.5-10 mmol/L L-glutamine (preferably 1-7 mmol/L, more preferably 2-6 mmol/L, even more preferably 3-5 mmol/L, still more preferably about 2 mmol/L);
(d) 0.01-1.0 mmol/L ascorbic acid (preferably 0.05-1.0 mmol/L, more preferably 0.1-0.5 mmol/L, even more preferably 0.2-0.4 mmol/L, still more preferably about 0.3 mmol/L);
(e) 1-100 ng/ml IGF-1 (preferably 2-90 ng/ml, more preferably 3-80 ng/ml, even more preferably 4-70 ng/ml, still more preferably 5-60 ng/ml, more preferably 6-50 ng/ml, more preferably 7-40 ng/ml, more preferably 8-30 ng/ml, more preferably 9-20 ng/ml, such as about 10 ng/ml); and
(f) 1-10 ng/ml TGFβ1 (preferably 1-9 ng/ml, more preferably 2-8 ng/ml, even more preferably 3-7 ng/ml, most preferably 4-6 ng/ml, and even most preferably about 5 ng/ml);

(iv) culturing the mixture obtained in step (iii) under mechanical stretching in a serum-free EHM culture medium as defined in step (iii) (a)-(f), whereby force-generating EHM is formed.

The minimum essential medium in step (i) may be selected from Iscove's medium, αMEM, DMEM, and RPMI. In a preferred embodiment, the basal medium is Iscove's medium or αMEM. In a more preferred embodiment, the basal medium is Iscove's medium. However any suitable minimal medium may be used in the method. Recipes of suitable minimum essential mediums are provided herein or are publicly available, e.g. from catalogues of the ATCC.

Preferably, the serum-free supplement of step (i) further comprises one or more components selected from the group consisting of vitamin A, D-galactose, linoleic acid, linolenic acid, progesterone, and putrescine. These components are conducive for the viability of the cells. Suitable concentrations of the respective components are known to the skilled person or can be easily determined using routine measures.

For the serum-free supplement referred to in component (b) of step (i), commercially available B27® supplement or B27® supplement minus insulin can be used. Alternatively, the custom made supplement as shown in Table 2 below can be used. In a preferred embodiment, the B27® supplement or B27® supplement minus insulin used as component (b) of step (i) of the above method is applied in an amount of 2-6% (v/v). More preferably, the B27® supplement or B27® supplement minus insulin used as component (b) of step (i) of the above method is applied in an amount of 4% (v/v).

Further, said reconstitution mixture of step (i) preferably comprises 0.3-0.5 mg collagen per $1.5 \times 10^6$ cardiac myocyte and non-myocyte cell mixtures. More preferably, said reconstitution mixture of step (i) comprises about 0.4 mg collagen per $1.5 \times 10^6$ cardiac myocyte and non-myocyte cell mixtures.

The collagen in component (c) of the reconstitution mixture of step (i) is preferably of medical grade and selected from the group consisting of collagen type I, collagen type III, collagen type V, and a mixture thereof. In a more preferred embodiment, component (c) of the reconstitution mixture of step (i) comprises at least 90% of said collagen is collagen type I. However, said collagen may also further comprises one or more extracellular matrix components selected from the group consisting of elastin, laminin, entactin, nidogen, proteoglycan, and fibronectin. Usually, the exact composition of the collagen will depend on the origin, from where it is derived from. The collagen is preferably of human origin, but bovine origin, or marine origin, such as from algae or fish origin, is also contemplated.

The development of functional (i.e force-generating), defined, serum-free human tissue engineered myocardium for potential regenerative heart therapy requires a number of hurdles to be overcome. Of paramount importance is a reliable source of human heart cells. To date, human pluripotent stem cells have emerged as the major source of human heart cell. Pluripotent stem cells are able to differentiate into every cell type of the body. As such, human pluripotent stem cells offer the unique opportunity to obtain bona fide human heart cells. Currently, the most utilized pluripotent cells are embryonic stem cells (ESC) or induced pluripotent stem cells (iPSC). Human ESC-lines were first established by Thomson and coworkers (Thomson et al. Science 282: 1145-1147 (1998); incorporated herein in its entirety by reference). Human ESC research recently enabled the development of a new technology to reprogram cells of the body into a ES-like cell. This technology was pioneered by Yamanaka and coworkers in 2006 (Takahashi & Yamanaka Cell 126: 663-676 (2006); incorporated herein in its entirety by reference). Resulting induced pluripotent cells (iPSC) show a very similar behavior as ESC and, importantly, are also able to differentiate into every cell of the body. Cardiac differentiation of ESCs and iPSCs occurs in embryoid body (Schroeder et al. Biotechnol Bioeng 92: 920-933 (2005); incorporated herein in its entirety by reference) cultures as a more or less stochastic event yielding cell populations containing 5-20% bona fide cardiomyocytes (Kehat et al. *J Clin Invest* 108: 407-414 (2001); Mummery et al. *Circulation* 107: 2733-2740 (2003); Xu et al. *Circ Res* 91: 501-508 (2002); all incorporated herein by reference). Moreover, it was reported that also parthenogenetic stem cells are likely to be suitable for EHM-production (Didié et al. J Clin Invest. doi:10.1172/JCI66584; incorporated herein in its entirety by reference). Accordingly, in a preferred embodiment, the cardiac myocytes are human cardiac myocytes. Preferably, said cardiac myocytes are derived from embryonic stem cells, wherein the cell is not produced using a process which involves modifying the germ line genetic identity of human beings or which involves use of a human embryo for industrial or commercial purposes. In an alternative embodiment, the cardiac myocytes are derived from induced pluripotent cells, parthogenetic stem cells, or adult stem cells, as described above.

Recently, several serum-free, cytokine-directed protocols for more efficient cardiac differentiations have been described (Burridge et al. *Cell Stem Cell* 10: 16-28 (2012); incorporated herein in its entirety by reference) yielding cultures containing up to 98% cardiomyocytes (Lian et al. *Proc Natl Acad Sci USA* (2012); incorporated herein in its entirety by reference). Accordingly, in another preferred embodiment, the cardiac myocytes can be obtained by serum-free differentiation. On the other hand, the cardiac myocytes may also be derived from non-human primate stem cells, fetal or neonatal cardiac myocytes.

It has been demonstrated that it is advantageous to provide the cardiac myocytes in admixture with cells of one or more class of cells selected from the group of non-myocytes such as fibroblasts, endothelial cells, smooth muscle cells, and mesenchymal stem cells. Hence, preferably the cardiac myocytes admixture contains 20-80% cardiac myocytes, more preferably 30-70% cardiac myocytes, even more preferably 40-60% cardiac myocytes, and most preferably about 50% cardiac myocytes, wherein the non-myocytes are fibroblasts or endothelial cells. Indeed, it is a particularly preferred embodiment that the non-myocytes are fibroblasts. Suitable non-myocytes may be identified by expression of e.g. the CD90 surface marker. Suitable cells can be identified, for example, using techniques such as immune staining or fluorescence activated cell sorting (FACS). EHMs resulting from such an admixture usually generate a higher force.

Preferably, the cardiac myocytes are provided in step (i) in a cell concentration of at least $2.7-20 \times 10^6$ per ml. However, in a more preferred embodiment, the cardiac myocytes are provided in step (i) in a cell concentration of at least $2.9-10 \times 10^6$ per ml, even more preferably in a cell concentration of at least $3.1-5 \times 10^6$ per ml, and in a most preferred embodiment in a cell concentration of at least $3.3-3.4 \times 10^6$ per ml.

The mould referred to in the method may have any suitable form allowing incorporation of the EHM in a host in need thereof. However, in a preferred embodiment, the mould is ring-, multiangular-, disc- or pouch-shaped.

Cell culturing is carried out using common procedures and equipment generally known in the art. Usually, culturing conditions comprise a temperature in the range of 30-40° C., preferably 36-38° C., and most preferably at about 37° C., using a humidified cell culture incubator in the presence of 5-10% $CO_2$.

For the serum-free supplement referred to in component (b) of step (iii), commercially available B27® supplement or B27® supplement minus insulin can be used. Alternatively, the custom made supplement as shown in Table 2 below can be used. In a preferred embodiment, the B27® supplement or B27® supplement minus insulin used as component (b) of step (iii) of the above method is applied in an amount of 2-6% (v/v). More preferably, the B27® supplement or B27® supplement minus insulin used as component (b) of step (i) of the above method is applied in an amount of 4% (v/v).

In addition, the serum-free supplement of step (iii) may further comprise one or more components selected from the group consisting of vitamin A, D-galactose, L-carnitine, linoleic acid, linolenic acid, progesterone, and putrescine. As noted above, these components are conducive for the viability of the cells. Suitable concentrations of the respective components are known to the skilled person or can be easily determined using routine measures.

The basal medium comprised in said EHM culture medium in step (iii) may be selected from Iscove's medium, αMEM, DMEM, and RPMI. Since RPMI usually has a lower concentration of calcium, it may be necessary to supplement the RPMI basal medium accordingly. If deemed appropriate, the basal medium may be supplemented with non-essential amino acids. If αMEM is used as the basal medium, the EHM culture medium need not be supplemented additionally with non-essential amino acids. The non-essential amino acids are commercially available as a combined supplement. Such a supplement for example comprises 750 mg/L glycine, 890 mg/L L-alanine, 1320 mg/L L-asparagine, 1330 mg/L L-aspartic acid, 1470 mg/L L-glutamic acid, 1150 mg/L L-proline, and 1050 mg/L L-serine.

In a preferred embodiment, the basal medium comprised in said EHM culture medium in step (iii) is Iscove's medium or αMEM. In a more preferred embodiment, the basal medium comprised in said EHM culture medium in step (iii) is Iscove's medium. However any basal medium may be used in the method. Recipes of suitable minimum essential mediums are provided herein or are publicly available, e.g. from catalogues of the ATCC.

As demonstrated in the Examples below, the serum-free EHM culture medium advantageously further comprises VEGF, FGF, or both VEGF and FGF. Addition of VEGF and/or FGF has been shown to result in EHM exhibiting a higher force.

Typically, VEGF is added in a concentration of about 5-20 ng/ml VEGF, preferably 6-18 ng/ml, more preferably 7-16 ng/ml, even more preferably 8-14 ng/ml, most preferably 9-12 ng/ml, and even most preferably in a concentration of about 10 ng/ml.

FGF is added in a concentration of about 5-20 ng/ml FGF, preferably 6-18 ng/ml, more preferably 7-16 ng/ml, even more preferably 8-14 ng/ml, most preferably 9-12 ng/ml, and even most preferably in a concentration of about 10 ng/ml.

In principle, any type of VEGF, FGF, IGF1 and TGFβ1 can be used, as long as these growth factors are capable of signalling via their corresponding receptors on the cell surface of the cardiac myocytes of the EHM. However, in a preferred embodiment the VEGF is human VEGF. In another preferred embodiment, the FGF is human FGF. In still another preferred embodiment IGF1 is human IGF1. In still another embodiment, the TGFβ1 is human TGFβ1. In a most preferred embodiment, all of VEGF, FGF, IGF1, and TGFβ1 are human.

Usually, culturing in step (iii) is carried out for at least 3 days, preferably for about 3 to about 7 days.

In principle, the further culturing in step (iv) may be carried out for any suitable period of time. However, usually, the further culturing in step (iv) is carried out for a period of at least 3-60 days, preferably for 4-30 days, more preferably for 5-20 days. In a most preferred embodiment, the further culturing is carried out for 7 days, since this time period represents an optimal balance of a preferably short culturing time and a time period which is sufficient to result in force-generating EHMs.

Usually, step (iv) of the above method is carried out on a stretch device, as generally known in the art. Preferably, the stretch device applies a static, phasic or dynamic stretch to the EHM. More specifically, mechanical stretching can be (i) static, (ii) dynamic, or (iii) flexible against a resilient load.

As will be further demonstrate below, the EHM produced by the above method generates more than 0.01 mN force upon induction with 3 mM calcium as determined using the method described in Zimmermann et al. Circ. Res. 90, 223-230 (2002), preferably more than 0.1 mN force, more preferably more than 0.2 mN force, and most preferably more than 0.3 mN force upon induction with 3 mM calcium as determined using the method described in Zimmermann et al. Circ. Res. 90, 223-230 (2002).

Another detailed prior art protocol which is suitable to serve as a basis for the improved method disclosed herein is described by Soong et al. Curr Prot Cell Biol. 55: 23.8.1-23.8.21 (2012), which is incorporated herewith in its entirety, and in particular reference is made to the "Basic Protocol 2", and the "Support Protocol 2".

TABLE 1

Comparison of protocols for human EHM generation.

| Component | Basic protocol | Matrix protocol | Serum-free protocol |
|---|---|---|---|
| Matrix | Rat tail collagen I (0.4 mg/EHM) Matrigel (10% v/v) | Medical grade bovine collagen (0.4 mg/EHM) | Medical grade bovine collagen (0.4 mg/EHM) |
| Concentrated medium (2x) | 2x DMEM 20% horse serum | 2x DMEM 40% FBS | 2x DMEM 8% B27 or 8% B27 minus insulin or custom made serum supplement (2x) |
| Culture medium | 4% chick embryo extract 200 U/ml Penicillin 200 mg/ml Streptomycin Iscove's | 200 U/ml Penicillin 200 mg/ml Streptomycin Iscove's | 200 U/ml Penicillin 200 mg/ml Streptomycin Basal medium (Iscove's, a MEM, RPMI) comprising 1-2 mmol/L $Ca^{2+}$ |
| | 20% FBS | 20% FBS | 4% B27 or 4% B27 minus insulin or custom made serum supplement |
| | 1% non-essential amino acids | 1% non-essential amino acids | 1% non-essential amino acids, omit if aMEM |
| | 2 mmol/L L-glutamine | 2 mmol/L L-glutamine | 2 mmol/L L-glutamine, omit if aMEM or if RPMI |
| | 0.3 mmol/L ascorbic acid | 0.3 mmol/L ascorbic acid | 0.3 mmol/L ascorbic acid, omit if aMEM |
| | 100 µmol/l β-mercaptoethanol | 100 µmol/l β-mercaptoethanol | 0.05% Fatty acids supplement 20 ng/ml IGF 10 ng/ml VEGF 10 ng/ml FGF 5 ng/ml TGFb1 day 0-3 |
| | 100 U/ml Penicillin 100 mg/ml Streptomycin | 100 U/ml Penicillin 100 mg/ml Streptomycin | 100 U/ml Penicillin 100 mg/ml Streptomycin |

TABLE 2

Custom-made supplement to replace B27.

| Substance | Final concentration | 25x | Supplier |
|---|---|---|---|
| Albumin | 5 mg/ml | 125 mg/ml | Sigma, A9511 |
| Transferrin | 10 µg/ml | 250 µg/ml | Sigma, T0665 |
| EthanolamineHCl | 2 µg/ml | 50 µg/ml | Sigma, E6133 |
| Sodium selenite | 0.032 µg/ml | 0.8 µg/ml | Sigma, S5361 |
| L-CarnitineHCl | 4 µg/ml | 100 µg/ml | Sigma, C0283 |
| Hydrocortisone | 1 µg/ml | 25 µg/ml | Sigma, H2270 |
| Fatty acid supplement | 0.5 µl/ml | 12.5 µl/ml | Sigma, F7050 |
| Triiodo-L-thyronine | 0.004 µg/ml | 0.1 µg/ml | Sigma, T 6397 |

Prepare 25x in cell culture-qualified water

TABLE 3

Iscove's basa medium formulation without glutamine (Biochrom).

| Substance | Concentration (mg/l) |
|---|---|
| NaCl | 4505 |
| KCl | 330 |
| NaH2PO4 | 125 |
| MgSO4•7H2O | 200 |
| CaCl2•2H2O | 218,6 |
| KNO3 | 0.076 |
| Na2SeO3 | 0.0173 |
| D-glucose | 4500 |
| HEPES | 5958 |
| NaHCO3 | 3024 |
| Phenol red | 15 |
| Na-pyruvate | 110 |
| L-arginine•HCl | 84 |
| L-histidine•HCl•H2O | 42 |
| Glycine | 30 |
| L-isoleucine | 105 |
| L-lysine•HCl | 146 |
| L-methionine | 30 |
| L-phenylalanine | 66 |
| L-leucine | 105 |
| L-threonine | 95 |
| L-tryptophane | 16 |
| L-tyrosine•2Na | 104.2 |
| L-serine | 42 |
| L-valine | 94 |
| L-cystine | 70 |
| L-asparagine | 25 |
| L-aspartic acid | 30 |
| L-alanine | 25 |
| L-glutamic acid | 75 |
| L-proline | 40 |
| Biotin | 0.013 |
| Vitamin B12 | 0.013 |
| Nicotin acid amide | 4 |
| Cholin chloride | 4 |
| D-Ca-pantothenate | 4 |
| Pyridoxal•HCl | 4 |
| Thiamine•HCl | 4 |
| Riboflavin | 0.4 |
| Folic acid | 4 |
| Myo-inositol | 7.2 |

TABLE 4

RPMI basal medium (Invitrogen, )

| Components | Molecular Weight | Concentration (mg/L) |
|---|---|---|
| AminoAcids | | |
| Glycine | 75 | 10 |
| L-Alanyl-Glutamine | 217 | 446 |
| L-Arginine | 174 | 200 |
| L-Asparagine | 132 | 50 |
| L-Aspartic acid | 133 | 20 |
| L-Cystine | 240 | 50 |
| L-Glutamic Acid | 147 | 20 |
| L-Histidine | 155 | 15 |
| L-Hydroxyproline | 131 | 20 |
| L-Isoleucine | 131 | 50 |
| L-Leucine | 131 | 50 |
| L-Lysine hydrochloride | 183 | 40 |
| L-Methionine | 149 | 15 |
| L-Phenylalanine | 165 | 15 |
| L-Proline | 115 | 20 |
| L-Serine | 105 | 30 |
| L-Threonine | 119 | 20 |
| L-Tryptophan | 204 | 5 |
| L-Tyrosine | 181 | 20 |
| L-Valine | 117 | 20 |
| Vitamins | | |
| Biotin | 244 | 0.2 |
| Choline chloride | 140 | 3 |
| D-Calcium pantothenate | 477 | 0.25 |
| Folic Acid | 441 | 1 |
| Niacinamide | 122 | 1 |
| Para-Aminobenzoic Acid | 137 | 1 |
| Pyridoxine hydrochloride | 206 | 1 |
| Riboflavin | 376 | 0.2 |
| Thiamine hydrochloride | 337 | 1 |
| Vitamin B12 | 1355 | 0.005 |
| i-Inositol | 180 | 35 |
| InorganicSalts | | |
| Calcium nitrate ($Ca(NO_3)_2 \cdot 4H_2O$) | 236 | 100 |
| Magnesium Sulfate ($MgSO_4$—$7H_2O$) | 246 | 100 |
| Potassium Chloride (KCl) | 75 | 400 |
| Sodium Bicarbonate ($NaHCO_3$) | 84 | 2000 |
| Sodium Chloride (NaCl) | 58 | 6000 |
| Sodium Phosphate dibasic ($Na_2HPO_4$) anhydrous | 142 | 800 |
| Other Components | | |
| D-Glucose (Dextrose) | 180 | 2000 |
| Glutathione (reduced) | 307 | 1 |
| Phenol Red | 376.4 | 5 |

TABLE 5

αMEM basal medium formulation (Invitrogen).

| Components | Molecular Weight | Concentration (mg/L) |
|---|---|---|
| AminoAcids | | |
| Glycine | 75 | 50 |
| L-Alanine | 89 | 25 |
| L-Alanyl-L-Glutamine | 203 | 406 |
| L-Arginine | 211 | 105 |
| L-Asparagine-H2O | 132 | 50 |
| L-Aspartic acid | 133 | 30 |
| L-Cysteine hydrochloride | 158 | 100 |
| L-Cystine | 240 | 24 |
| L-Glutamic Acid | 147 | 75 |
| L-Histidine | 155 | 31 |
| L-Isoleucine | 131 | 52.4 |
| L-Leucine | 131 | 52.4 |
| L-Lysine | 146 | 58 |
| L-Methionine | 149 | 15 |
| L-Phenylalanine | 165 | 32 |
| L-Proline | 115 | 40 |
| L-Serine | 105 | 25 |
| L-Threonine | 119 | 4 |
| L-Tryptophan | 204 | 10 |
| L-Tyrosine | 181 | 36 |
| L-Valine | 117 | 46 |
| Vitamins | | |
| Ascorbic Acid | 176 | 50 |
| Biotin | 244 | 0.1 |
| Choline chloride | 140 | 1 |
| D-Calcium pantothenate | 477 | 1 |
| Folic Acid | 441 | 1 |
| Niacinamide | 122 | 1 |
| Pyridoxal hydrochloride | 204 | 1 |
| Riboflavin | 376 | 0.1 |
| Thiamine hydrochloride | 337 | 1 |
| Vitamin B12 | 1355 | 1.36 |
| i-Inositol | 180 | 2 |

TABLE 5-continued

αMEM basal medium formulation (Invitrogen).

| Components | Molecular Weight | Concentration (mg/L) |
|---|---|---|
| InorganicSalts | | |
| Calcium chloride ($CaCl_2$ —$2H_2O$) | 147 | 264 |
| Magnesium Sulfate ($MgSO_4$ —$7H_2O$) | 246 | 200 |
| Potassium Chloride (KCl) | 75 | 400 |
| Sodium Bicarbonate (NaHCOa) | 84 | 2200 |
| Sodium Chloride (NaCl) | 58 | 6800 |
| Sodium Phosphate monobasic ($Na_2HPO_4$—$2H_2O$) | 156 | 158 |
| Other Components | | |
| D-Glucose (Dextrose) | 180 | 1000 |
| Lipoic Acid | 206 | 0.2 |
| Phenol Red | 376.4 | 10 |
| Sodium Pyruvate | 110 | 110 |

TABLE 6

Serum-free, defined medium for EHM generation.

| Substance | Concentration | Supplier |
|---|---|---|
| Iscove's | | Biochrom, F0465 |
| B27 supplement or B27 supplement minus insulin or custom-made supplement | 4% | Invitrogen, 17504044 or 0050129SA |
| Non-essential amino acids | 1% | Invitrogen, 11140035 |
| L-Glutamine | 2 mmol/L | Invitrogen 25030-081 |
| Penicillin/Streptomycin | 100 U/ml/100 mg/ml | Invitrogen, 15070-063 |
| Ascorbic acid | 0.3 mmol/L | Sigma, A8960 |
| hFGF | 10 ng/ml | Peprotech, AF-100-18B |
| hIGF | 20 ng/ml | Peprotech, AF-100-11 |
| hVEGF | 10 ng/ml | Peprotech, AF-100-20 |
| hTGF-β1, day 0-3 | 5 ng/ml | Peprotech, 100-21 |
| Bovine collagen, acid soluble DM6 | 0.8 mg/ml | Devros Medical |

TABLE 7

Alternative serum-free, defined medium for EHM generation.

| Substance | Concentration | Supplier |
|---|---|---|
| αMEM | | Invitrogen, 32561-029 |
| B27 supplement or B27 supplement minus insulin or custom-made supplement | 4% | Invitrogen, 17504044 or 0050129SA |
| Penicillin/Streptomycin | 100 U/ml/100 mg/ml | Invitrogen, 15070-063 |
| hFGF | 10 ng/ml | Peprotech, AF-100-18B |
| hIGF | 20 ng/ml | Peprotech, AF-100-11 |
| hVEGF | 10 ng/ml | Peprotech, AF-100-20 |
| hTGF-β1, day 0-3 | 5 ng/ml | Peprotech, 100-21 |
| Bovine collagen, acid soluble DM6 | 0.8 mg/ml | Devros Medical |

The invention is further described by the following embodiments:

1. A method for producing engineered heart muscle (EHM), the method comprising the steps of:
   (i) providing a serum-free reconstitution mixture in one or more moulds, said reconstitution mixture comprising (a) a serum-free minimum essential medium; (b) a serum-free supplement resulting in a final concentration of 0.5-50 mg/ml albumin, 1-100 μg/ml transferrin, 0.1-10 μg/ml ethanol amine, 0.003-0.3 μg/ml sodium selenite, 0.4-40 μg/ml L-Carnitine HCl, 0.1-10 μg/ml Hydrocortisone, 0.05-5 μl/ml Fatty acid supplement, 0.0001-0.1 μg/ml triodo-L-thyronine (T3) and 0.2-2 mg/ml collagen; and (c) a mixture of human cardiac myocytes and human non-myocytes, wherein 20 to 80% of the total cell mixture are cardiac myocytes; wherein the reconstitution mixture has a pH of 7.2 to 7.6;
   (ii) culturing the serum-free reconstitution mixture in said one or more moulds, whereby the serum-free reconstitution mixture is allowed to condense for at least 15 min;
   (iii) culturing the mixture obtained in step (ii) in said one or more moulds in a serum-free EHM culture medium until the mixture condenses to at least 50% of its original thickness, wherein said EHM culture medium comprises (a) a basal medium comprising 0.5-3 mmol/L $Ca^{2+}$; (b) a serum-free supplement as defined in (i)(b); (c) 0.5-10 mmol/L L-glutamine; (d) 0.01-1.0 mmol/L ascorbic acid; (e) 1-100 ng/ml IGF-1; and (f) 1-10 ng/ml TGFβ1;
   (iv) culturing the mixture obtained in step (iii) under mechanical stretching in a serum-free EHM culture medium as defined in step (iii) (a)-(f), whereby force-generating EHM is formed.

2. The method of embodiment 1, wherein the minimum essential medium in step (i) is selected from Iscove's medium, αMEM, DMEM, and RPMI.

3. The method of embodiment 2, wherein the basal medium is Iscove's medium or αMEM.

4. The method of embodiment 2, wherein the basal medium is Iscove's medium.

5. The method of any one of embodiment 1-4, wherein the serum-free supplement of step (i) further comprises one or more components selected from the group consisting of vitamin A, D-galactose, linoleic acid, linolenic acid, progesterone, and putrescine.

6. The method of any one of embodiment 1-5, wherein the serum-free supplement in component (b) of step (i) is B27® supplement or B27® supplement minus insulin.

7. The method of embodiment 6, wherein the serum-free supplement in component (b) of step (i) is 2-6% (v/v) B27® supplement or B27® supplement minus insulin.

8. The method of embodiment 6, wherein the serum-free supplement in component (b) of step (i) is 4% (v/v) B27® supplement or B27® supplement minus insulin.

9. The method of any one of embodiment 1-8, wherein said reconstitution mixture of step (i) comprises 0.3-0.5 mg collagen per $1.5 \times 10^6$ cardiac myocyte and non-myocyte cell mixtures.

10. The method of embodiment 9, wherein said reconstitution mixture of step (i) comprises about 0.4 mg collagen per $1.5 \times 10^6$ cardiac myocyte and non-myocyte cell mixtures.

11. The method of any one of embodiment 1-10, wherein in component (c) of the reconstitution mixture of step (i) said collagen is selected from the group consisting of collagen type I, collagen type III, collagen type V, and a mixture thereof.

12. The method of any one of embodiment 1-11, wherein in component (c) of the reconstitution mixture of step (i) at least 90% of said collagen is collagen type I.

13 The method of any one of embodiment 1-12, wherein in component (c) of the reconstitution mixture of step (i) said collagen is of medical grade.

14 The method of any one of embodiment 1-13, wherein in component (c) of the reconstitution mixture of step (i) said collagen is of human origin, bovine origin, or marine origin.

15 The method of any one of embodiment 1-14, wherein in component (c) of the reconstitution mixture of step (i) said collagen further comprises one or more extracellular matrix components selected from the group consisting of elastin, laminin, entactin, nidogen, proteoglycan, and fibronectin.

16 The method of any one of embodiment 1-15, wherein the reconstitution mixture of step (i) has a pH of 7 to 7.8.

17 The method of embodiment 13, wherein the reconstitution mixture of step (i) has a pH of about 7.4.

18 The method of any one of embodiment 1-17, wherein the cardiac myocytes are human cardiac myocytes.

19 The method of any one of embodiment 1-18, wherein the cardiac myocytes are derived from embryonic stem cells, wherein the cell is not produced using a process which involves modifying the germ line genetic identity of human beings or which involves use of a human embryo for industrial or commercial purposes.

20 The method of any one of embodiment 1-19, wherein the cardiac myocytes are derived from induced pluripotent cells, parthogenetic stem cells, or adult stem cells.

21 The method of any one of embodiment 1-20, wherein the cardiac myocytes are obtained by serum-free differentiation.

22 The method of any one of embodiment 1-21, wherein the cardiac myocytes are non-human primate stem cell-derived, fetal or neonatal cardiac myocytes.

23 The method of any one of embodiment 1-22, wherein the cardiac myocytes are provided in admixture with cells of one or more class of cells selected from the group of non-myocytes such as fibroblasts, endothelial cells, smooth muscle cells, and mesenchymal stem cells.

24 The method of embodiment 23, wherein the cardiac myocytes admixture contains 20-80% cardiac myocytes.

25 The method of embodiment 23, wherein the cardiac myocytes admixture contains 30-70% cardiac myocytes.

26 The method of embodiment 23, wherein the cardiac myocytes admixture contains 40-60% cardiac myocytes.

27 The method of embodiment 23, wherein the cardiac myocytes admixture contains 50% cardiac myocytes.

28 The method of any one of embodiment 1-27, wherein the non-myocytes are fibroblasts or endothelial cells.

29 The method of any one of embodiment 1-28, wherein the non-myocytes are fibroblasts.

30 The method of any one of embodiment 1-29, wherein the non-myocytes express CD90.

31 The method of any one of embodiment 1-30, wherein the cardiac myocytes are provided in step (i) in a cell concentration of at least $2.7\text{-}20\times10^6$ per ml.

32 The method of embodiment 31, wherein the cardiac myocytes are provided in step (i) in a cell concentration of at least $2.9\text{-}10\times10^6$ per ml.

33 The method of embodiment 31, wherein the cardiac myocytes are provided in step (i) in a cell concentration of at least $3.1\text{-}5\times10^6$ per ml.

34 The method of embodiment 31, wherein the cardiac myocytes are provided in step (i) in a cell concentration of at least $3.3\text{-}3.4\times10^6$ per ml.

35 The method of any one of embodiment 1-34, wherein in step (ii) the mould is ring-, multiangular-, disc- or pouch-shaped.

36 The method of any one of embodiment 1-35, wherein culturing in step (ii) is carried out for 0.25-3 h.

37 The method of embodiment 36, wherein culturing in step (ii) is carried out for 0.5-1.5 h.

38 The method of any one of embodiment 1-37, wherein culturing is carried out at a temperature range of 30-40° C.

39 The method of embodiment 38, wherein culturing is carried out at a temperature range of 36-38° C.

40 The method of embodiment 39, wherein culturing is carried out at about 37° C.

41 The method of any one of embodiment 1-40, wherein culturing is carried out in a humidified cell culture incubator in the presence of 5-10% $CO_2$.

42 The method of any one of embodiment 1-41, wherein the serum-free supplement in component (b) of step (iii) is B27® supplement or B27® supplement minus insulin.

43 The method of embodiment 42, wherein the serum-free supplement in component (b) of step (iii) is 2-6% (v/v) B27® supplement or B27® supplement minus insulin.

44 The method of embodiment 43, wherein the serum-free supplement in component (b) of step (iii) is 4% (v/v) B27® supplement or B27® supplement minus insulin.

45 The method of any one of embodiment 1-44, wherein said serum-free supplement of step (iii) further comprises one or more components selected from the group consisting of vitamin A, D-galactose, L-carnitine, linoleic acid, linolenic acid, progesterone, and putrescine.

46 The method of any one of embodiment 1-45, wherein the basal medium comprised in said EHM culture medium in step (iii) is selected from Iscove's medium, αMEM, DMEM, and RPMI.

47 The method of embodiment 46, wherein the basal medium is Iscove's medium or αMEM.

48 The method of embodiment 47, wherein the basal medium is Iscove's medium.

49 The method of any one of embodiment 1-48, wherein the serum-free EHM culture medium comprises about 20 ng/ml IGF1.

50 The method of any one of embodiment 1-49, wherein the IGF1 is human IGF1.

51 The method of any one of embodiment 1-50, wherein the serum-free EHM culture medium comprises about 5 ng/ml TGFβ1.

52 The method of any one of embodiment 1-51, wherein the TGFβ1 is human TGFβ1.

53 The method of any one of embodiment 1-52, wherein the serum-free EHM culture medium further comprises VEGF, FGF, or both VEGF and FGF.

54 The method of any one of embodiment 1-53, wherein the VEGF is human VEGF.

55 The method of any one of embodiment 1-54, wherein the FGF is human FGF.

56 The method of embodiment 53, wherein the serum-free EHM culture medium comprises about 5-20 ng/ml VEGF.

57 The method of embodiment 56, wherein the serum-free EHM culture medium comprises about 10 ng/ml VEGF.

58 The method of embodiment 53, wherein the serum-free EHM culture medium comprises about 5-20 ng/ml FGF.

59 The method of embodiment 58, wherein the serum-free EHM culture medium comprises about 10 ng/ml FGF.

60 The method of any one of embodiment 1-59, wherein the serum-free EHM culture medium in step (iii) additionally comprises 750 mg/L glycine, 890 mg/L L-alanine, 1320 mg/L L-asparagine, 1330 mg/L L-aspartic acid, 1470 mg/L L-glutamic acid, 1150 mg/L L-proline, and 1050 mg/L L-serine.

61 The method of any one of embodiment 1-60, wherein culturing in step (iii) is carried out for at least 3 days.

62 The method of embodiment 61, wherein culturing in step (iii) is carried out for about 3 to about 7 days.

63 The method of any one of embodiment 1-62, wherein the culturing in step (iv) is carried out for a period of at least 3-60 days.

64 The method of embodiment 63, wherein the further culturing is carried out for 4-30 days.

65 The method of embodiment 63, wherein the further culturing is carried out for 5-20 days.

66 The method of embodiment 63, wherein the further culturing is carried out for 6-10 days.

67 The method of embodiment 63, wherein the further culturing is carried out for 7 days.

68 The method of any one of embodiment 1-67, wherein step (iv) is carried out on a stretch device.

69 The method of embodiment 68, wherein the stretch device applies a static, phasic or dynamic stretch.

70 The method of any one of embodiment 1-69, wherein said EHM generates more than 0.01 mN force upon induction with 3 mM calcium as determined using the method described in Zimmermann et al. Circ. Res. 90, 223-230 (2002).

71 The method of embodiment 70, wherein said EHM generates more than 0.1 mN force upon induction with 3 mM calcium as determined using the method described in Zimmermann et al. Circ. Res. 90, 223-230 (2002).

72 The method of embodiment 70, wherein said EHM generates more than 0.2 mN force upon induction with 3 mM calcium as determined using the method described in Zimmermann et al. Circ. Res. 90, 223-230 (2002).

73 The method of embodiment 70, wherein said EHM generates more than 0.3 mN force upon induction with 3 mM calcium as determined using the method described in Zimmermann et al. Circ. Res. 90, 223-230 (2002).

(B) Contractile force of hEHM generated with 100% cardiomyocytes (CM 100%) and a mixture of 70% cardiomyocytes and 30% cardiac fibroblasts (CM/CF 70/30%), n=1.

Figure 4A:
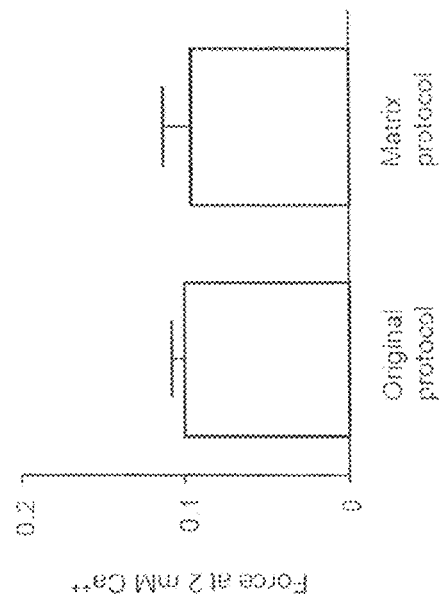
Figure 4B:
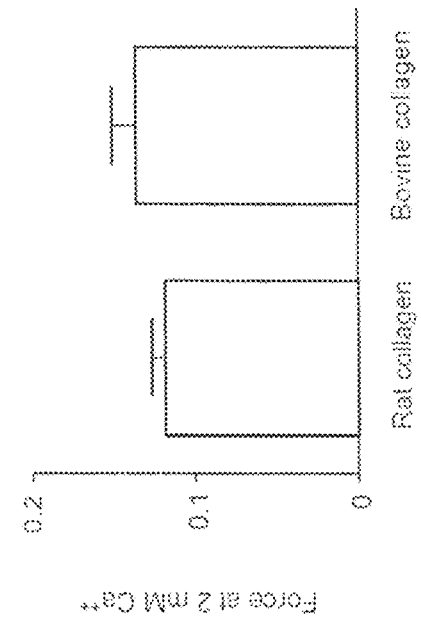
Figure 4C:
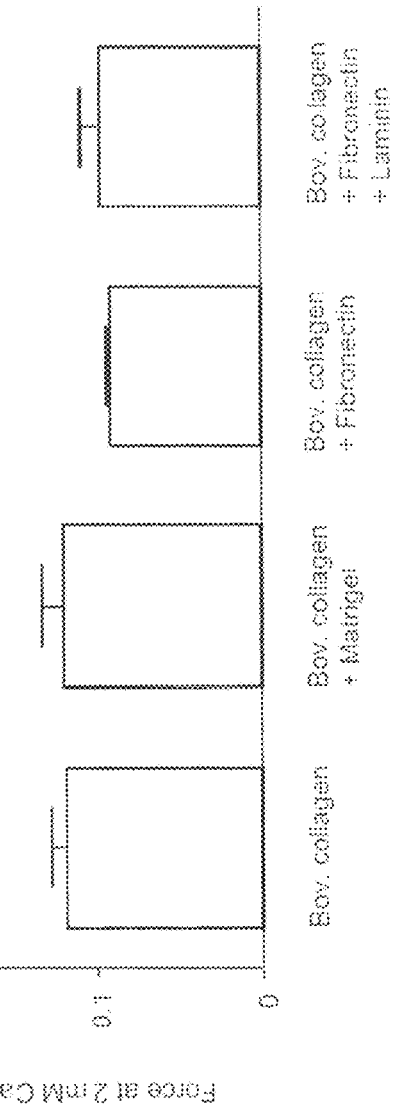

FIGS. 4A-4C. GMP-compatible hydrogel matrix. (A) Contractile force of hEHMs made with rat collagen (0.4 mg/EHM, n=12) or bovine collagen (0.4 mg/EHM, n=14) at an extracellular calcium concentration of 2 mmol/L. (B) Contractile force at 2 mmol/L extracellular calcium of hEHMs made with the "Original protocol" (rat collagen, Matrigel®, n=12) and the "Matrix protocol" (bovine collagen, no Matrigel®, n=9). Please refer also to Table 1. (C) Contractile force at 2 mmol/L extracellular calcium of hEHMs made with bovine (bov.) collagen only, bovine collagen plus Matrigel (10% v/v), bovine collagen plus fibronectin (5 µg/EHM), and bovine collagen plus fibronectin (5 µg/EHM) plus laminin (5 µg/EHM), n=4/group.

Figure 5A:
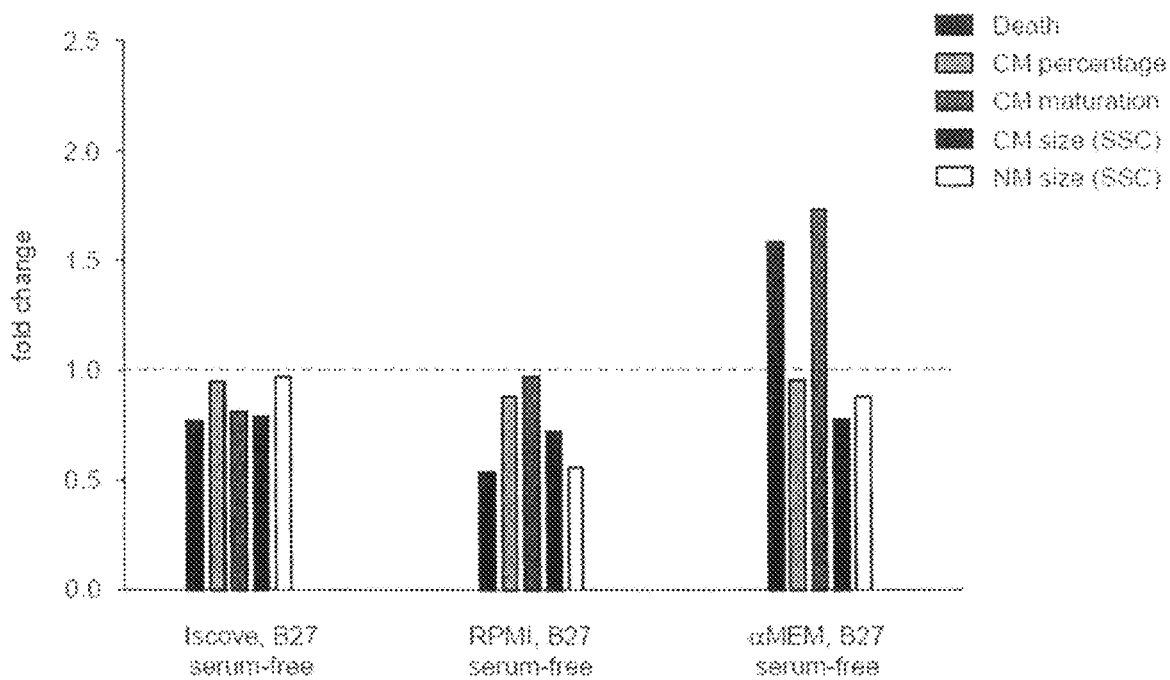
Figure 5B:
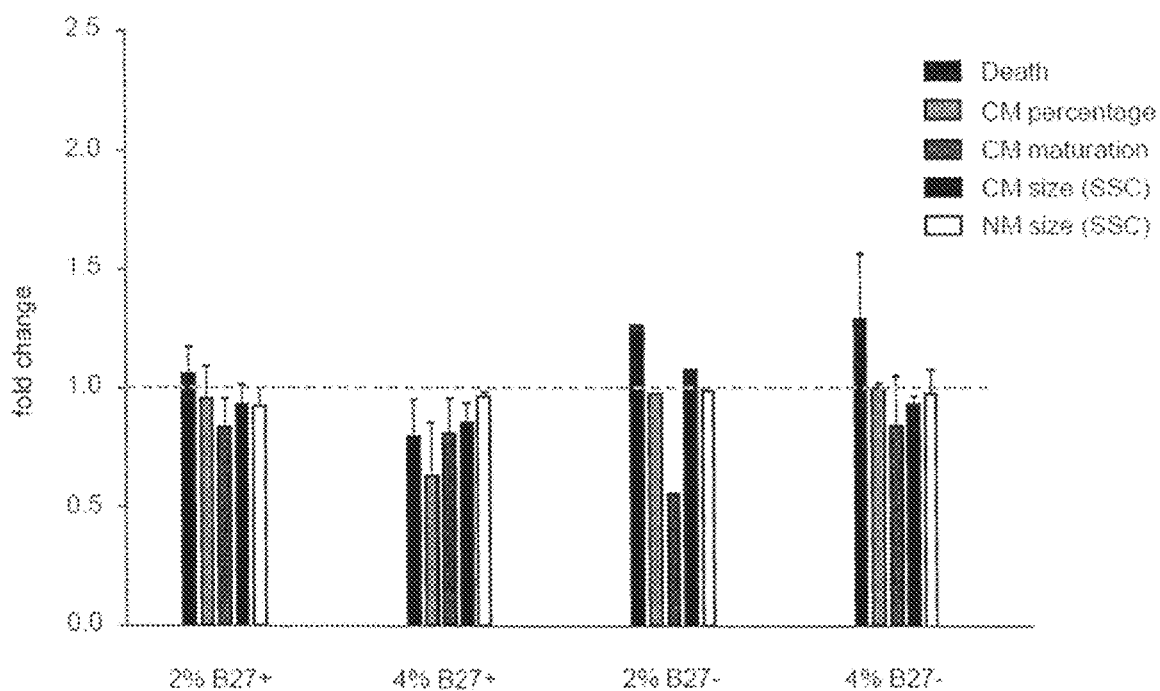

FIGS. 5A-5B. Screening of basal media and serum-free growth supplement vs. Iscove with 20% serum. (A) F.l.t.r.: Change in cell death, cardiomyocyte percentage (CM percentage), cardiomyocyte mean actinin fluorescence (CM maturation), cardiomyocyte size based on sideward scatter area (CM size) and non-myocyte size based on sideward scatter area (NM size) of serum free media based on Iscove's, RPMI and αMEM basal media (see also Table 2-4) compared to serum containing EHM medium (see also Table 1).

(B) F.l.t.r.: Change in cell death, cardiomyocyte percentage (CM percentage), cardiomyocyte mean actinin fluorescence (CM maturation), cardiomyocyte size based on sideward scatter area (CM size) and non-myocyte size based on sideward scatter area (NM size) of serum free media with 2% and 4% B27 plus insulin (B27+) and minus insulin (B27-) compared to serum containing EHM medium (see also Table 1).

Figure 6A:
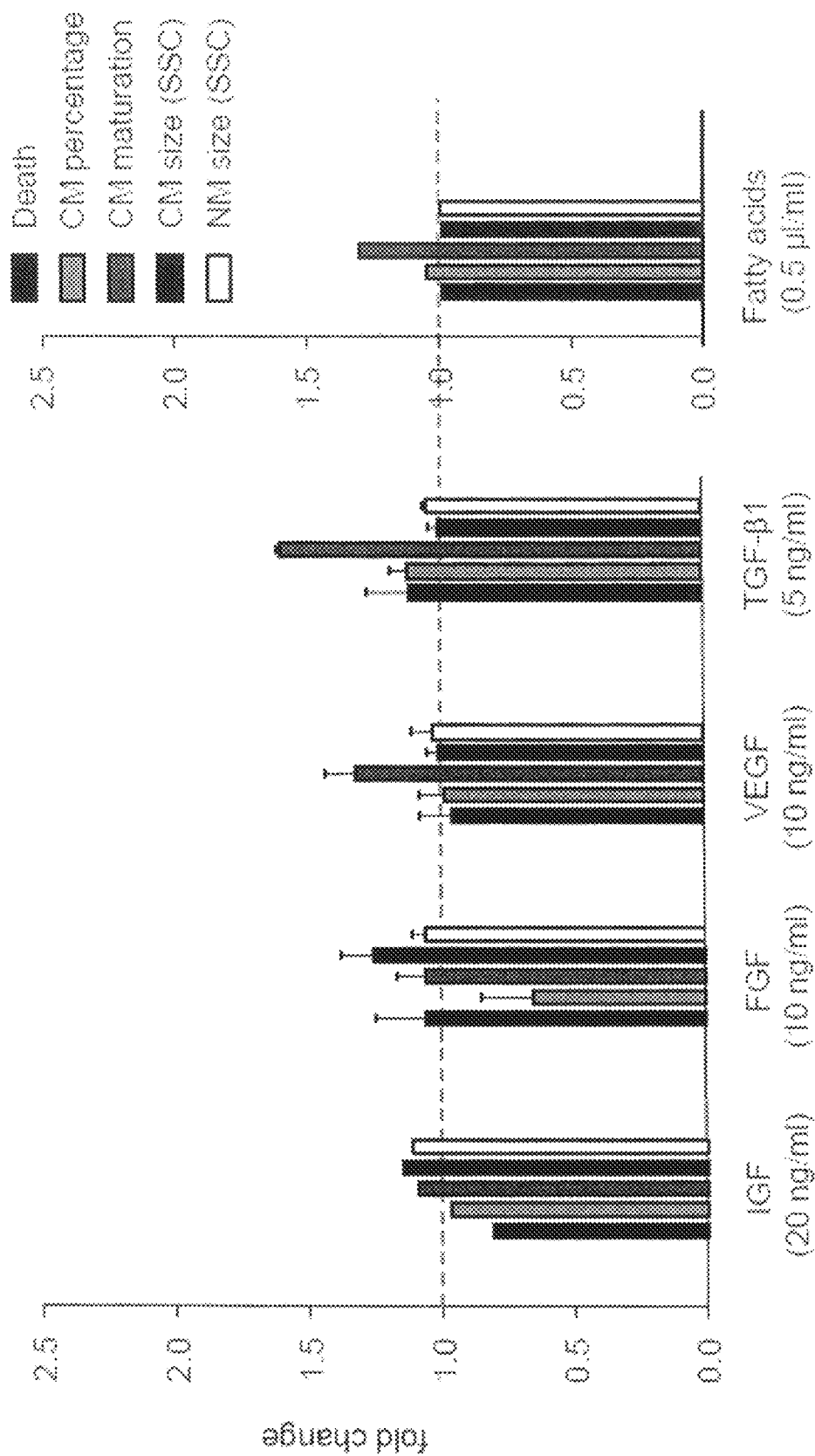
Figure 6B:
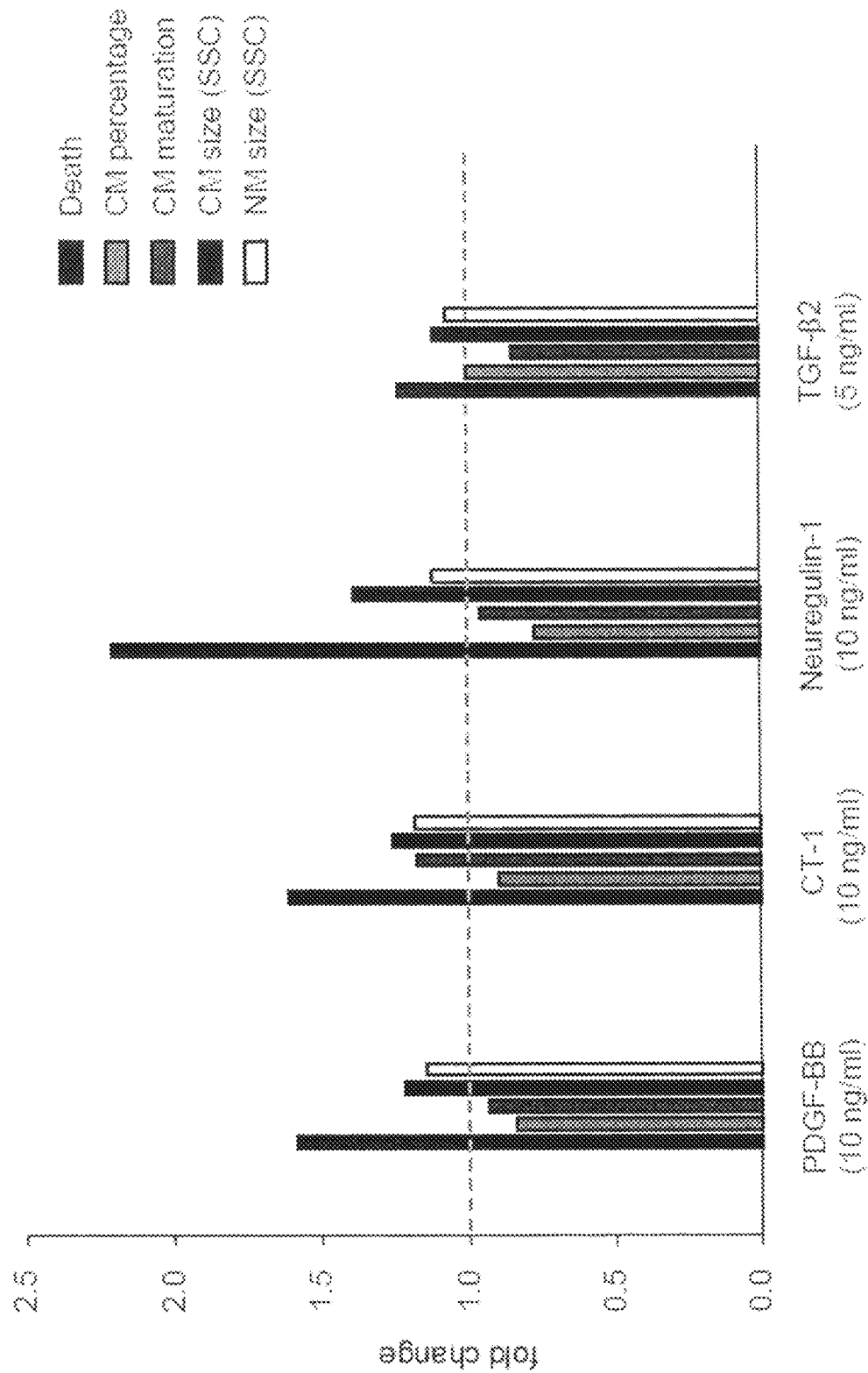

FIGS. 6A-6B. Screening of peptide growth factors and fatty acid supplement. (A) Factors considered for serum-free, defined EHM medium. F.l.t.r.: Change in cell death, cardiomyocyte percentage (CM percentage), cardiomyocyte mean actinin fluorescence (CM maturation), cardiomyocyte size based on sideward scatter area (CM size) and non-myocyte size based on sideward scatter area (NM size) by indicated growth factors and fatty acid supplement compared to serum free medium without the factor. (B) Factors not considered for serum-free, defined EHM medium. F.l.t.r.: Change in cell death, cardiomyocyte percentage (CM percentage), cardiomyocyte mean actinin fluorescence (CM maturation), cardiomyocyte size based on sideward scatter area (CM size) and non-myocyte size based on sideward scatter area (NM size) by indicated growth factors and fatty acid supplement compared to serum free medium without the factor.

FIGS. 7A-7D. Serum-free, defined EHM generation from hESC cells. (A) Contractile force of hEHMs (hES2) with increasing concentrations of extracellular calcium, comparison of serum-containing medium (Serum), and serum-free Iscove's-based medium (SF-IMDM, see also Table 5), serum-free αMEM-based medium (SF-αMEM, see also Table 6), and serum-free RPMI-based medium (SF-RPMI). Respective $EC_K$ for calcium, n=15/5/6/7 for Serum/SF IMDM, SF-αMEM, SF-RPMI, n.d. not determined. (B) Immunostaining of serum-free hEHM, showing typical heart muscle properties (muscle bundles). Staining was performed with an antibody against α-sarcomeric actinin and with DAPI for nuclear staining. (C) Percent change in force after adrenergic stimulation with 1 µM isoprenaline of serum-containing EHM (Serum), and serum-free Iscove's-based EHM (SF-IMDM), serum-free αMEM-based EHM (SF- αMEM), n=15/5/6, *p<0.05 (D) Percent change in force after muscarinic stimulation with 10 μM carbachol of serum-containing EHM (Serum), and serum-free Iscove's-based EHM (SF-IMDM), serum-free αMEM-based EHM (SF-αMEM), n=15/5/6. Bar: 20 μm FIGS. 8A-8B. Effect of calcium on serum-free hEHM force. A) Contractile force of hEHMs (hES2) with increasing concentrations of extracellular calcium, comparison of RPMI medium (~0.4 mM calcium, n=2), and RPMI medium with addition of 0.8 mM CaCl (final free calcium concentration ~1.2 mM calcium, n=2), B) Response to 1 μM isoprenaline of serum-free hEHM cultured in RPMI or RPMI+calcium medium.

Figure 9A:
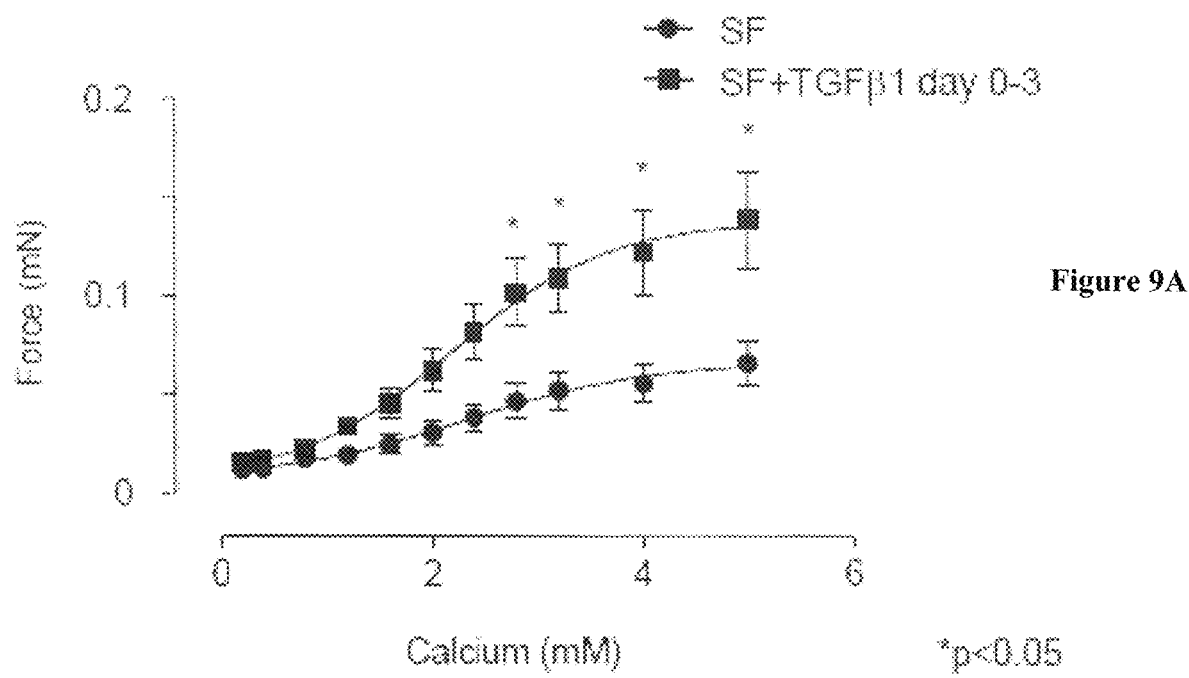
Figure 9B:
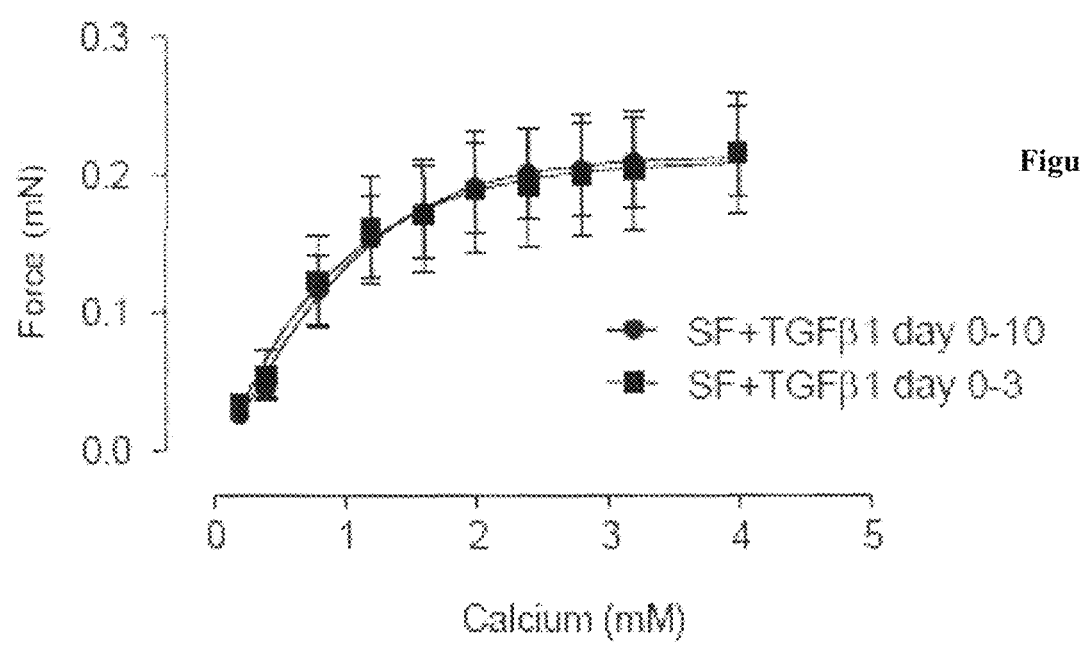

FIGS. 9A-9B. Effect of TGFb1 on hEHM force. (A) Contractile force of hEHMs (iPS BJ) with increasing concentrations of extracellular calcium, comparison of serum-free medium (SF), and serum-free medium with 5 ng/ml TGFb1 from culture day 0-3 (n=4/group, *p<0.05). (B) Comparison of contractile force of human EHM (hES2) in serum-free medium with TGFb1 treatment from culture 0-3 (SF+TGFb1 day 0-3) and culture day 0-10 (SF+TGFb1 day 0-10, n=5/group).

Figure 10:
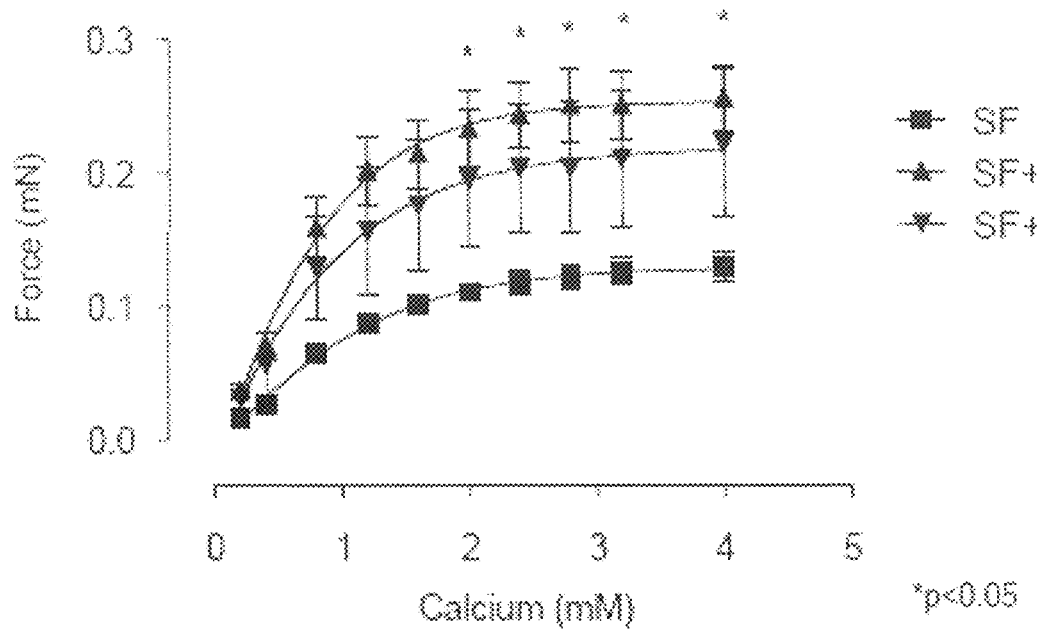

FIG. 10. Effect of FGF and VEGF on hEHM force. Contractile force of hEHMs (hES2) with increasing concentrations of extracellular calcium, comparison of serum-free medium (SF, n=3), serum-free medium with 10 ng/ml FGF-2 (SF+FGF, n=3), and serum-free medium with 10 ng/ml VEGF (SF+VEGF, n=3), *p<0.05 SF+FGF vs SF.

Figure 11:
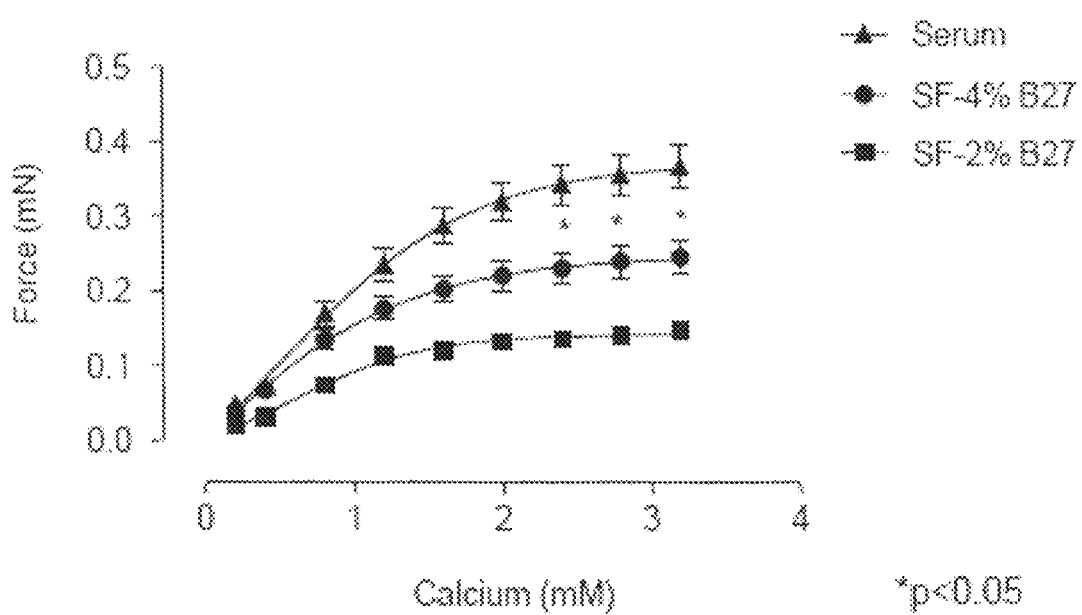

FIG. 11. Effect of B27 supplement concentration on hEHM force. Contractile force of hEHMs (hES2) with increasing concentrations of extracellular calcium, comparison of serum-containing medium (Serum), and serum-free medium with 2% B27 (SF-2% B27) and serum-free medium with 4% B27 (SF-4% B27), n=17/9/11, *p<0.05 vs 2% B27.

Figure 12:
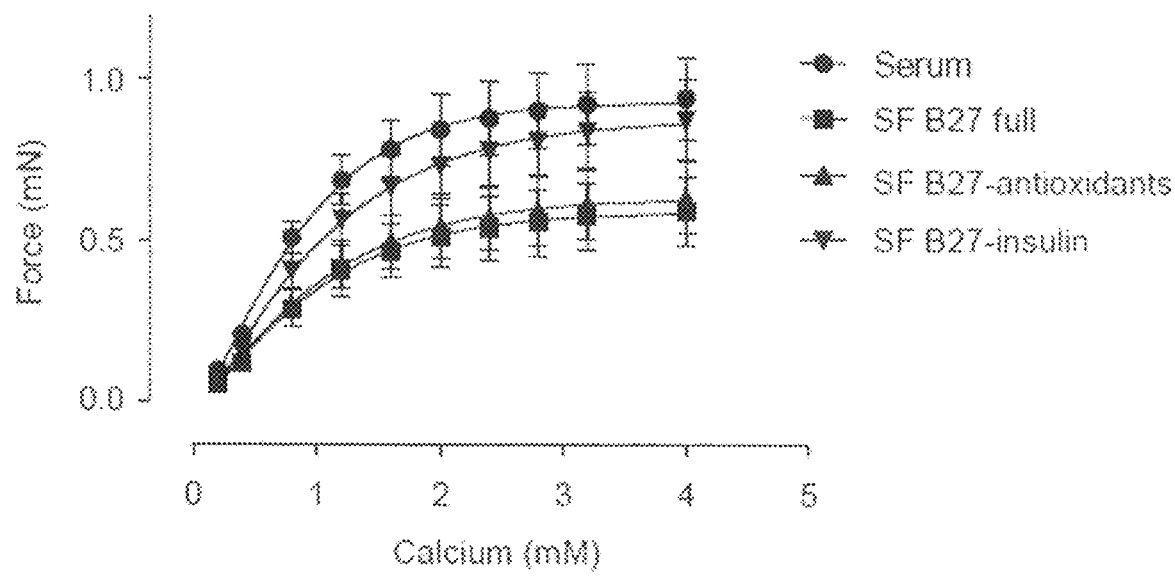

FIG. 12. Effect of B27 composition on hEHM force. Contractile force of hEHMs (hES2) with increasing concentrations of extracellular calcium, comparison of serum-containing medium (n=9), serum-free medium with full B27 (n=5), serum-free medium with B27 minus antioxidants (n=5), and serum-free medium with B27 minus insulin (n=5).

Figure 13A:
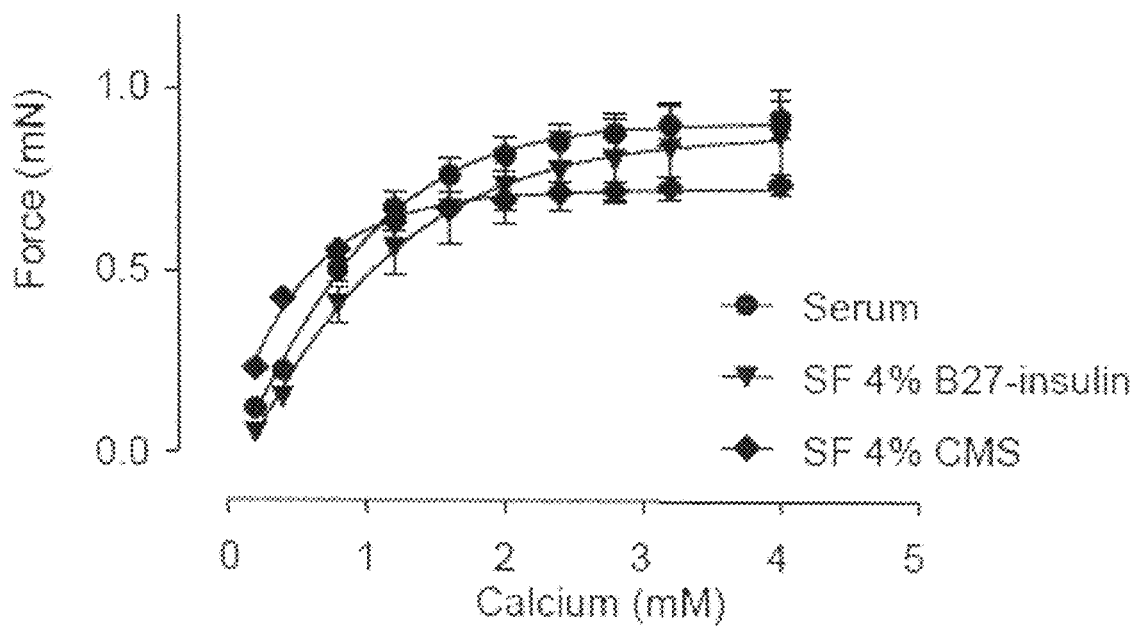
Figure 13B:
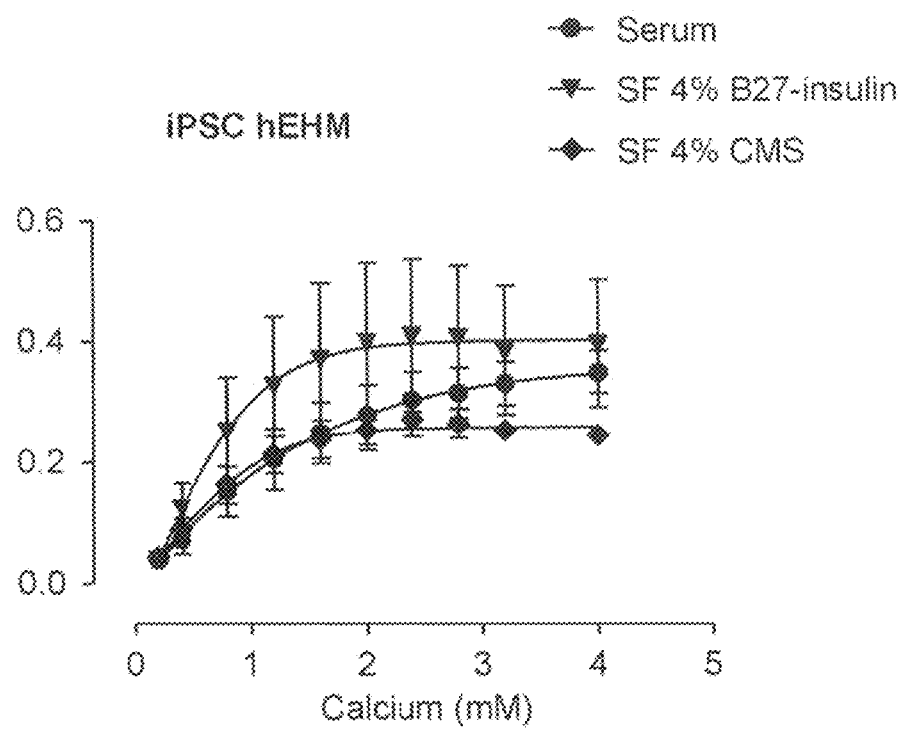

FIGS. 13A-13B. Replacement of B27 by custom-made supplement in hEHM from hES and iPS cells. (A) Contractile force of hEHMs (hES2) with increasing concentrations of extracellular calcium, comparison of serum-containing medium (n=3), serum-free medium with B27 minus insulin (B27-insulin, n=5), and serum-free medium with custom-made supplement (CMS; n=3). (B) Contractile force of hEHMs from iPS cells (BJ) with increasing concentrations of extracellular calcium, comparison of serum-containing medium (n=8), serum-free medium with B27-insulin (n=8), and serum-free medium with custom-made supplement (CMS; n=4).

Figure 14A:
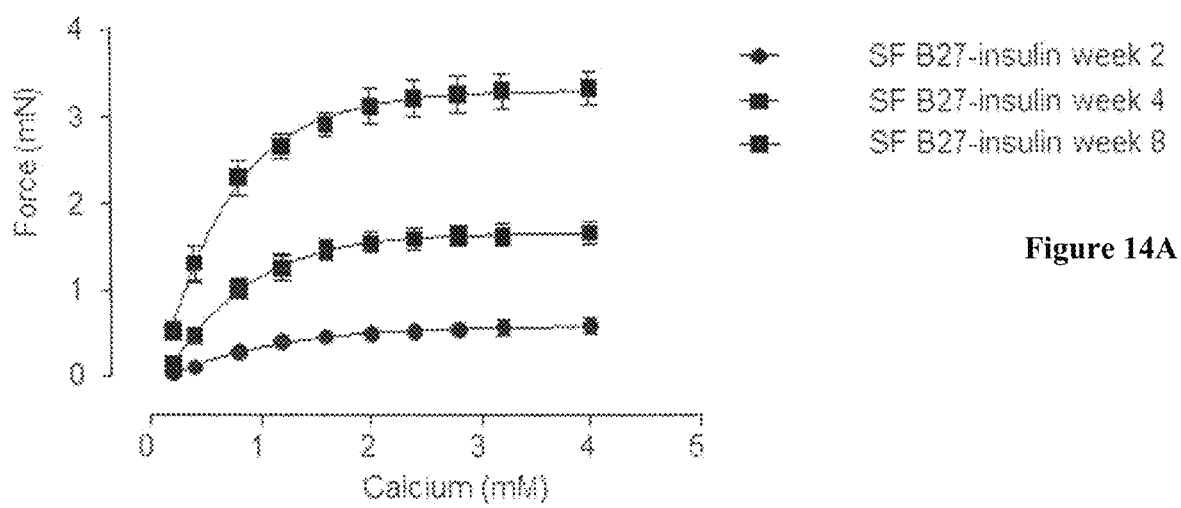
Figure 14B:
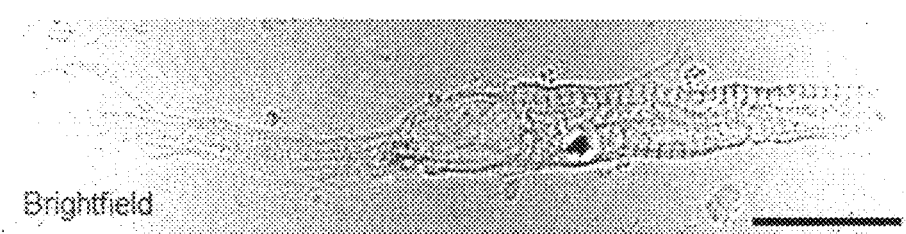

FIGS. 14A-14B. Maturation of serum-free hEHM with prolonged culture time. (A) Contractile force of hEHMs (hiPS-G1) at 2 week (lower graph), 4 week (middle graph), and 8 week (upper graph) time point of culture under serum-free conditions (n=4-6 per condition). (B) Brightfield image of individual cardiomyocyte from 8 week old serum-free EHM. Bar: 20 μm.

The following examples are meant to further illustrate, but not limit the invention. The examples comprise various technical features, and it will be appreciated that the invention also relates to combinations of the technical features presented in this exemplifying section.

EXAMPLES

Materials

The materials used herein are commercially available. For example, DMEM, RPMI, αMEM (cat. No. 32561-029), streptomycin, penicillin, and B27 are obtainable from Invitrogen; bovine collagen of medical grade is available from Devros Medical; fatty acid supplement can be ordered from Sigma (cat. No. F7050); and the various growth factors are available from Peprotech (FGF2, AF-1ββ-18B; IGF-1, AF-100-11; TGFβ1, 100-21).

Methods

Human ESC and iPS-Lines and Culture

The inventors utilized H9.2 (Technion, Haifa, Israel), hES3 (Embryonic Stem Cell International, Singapore) and transgenic hES3-ENVY (Costa, M., et al. Nat Methods 2: 259-260 (2005)) as well as hES2 line (McEwen Centre for Regenrative Medicine, Toronto, Canada; Yang et al. Nature 453: 524-528 (2008)) in the present study (approval by the Robert-Koch-Institute to W.-H.Z.: permit #12; reference number: 1710-79-1-4-16). Differentiated EBs were shipped to Hamburg/Goettingen at room temperature and arrived within 72-96 hrs. iPS lines were from Toronto (iPS BJ) and Goettingen (iPS 12, Streckfuss-Bomeke et al. Eur Heart J (2012) doi: 10.1093/eurheartj/ehs203, and iPS Sendai).

EBs were digested with collagenase B (1 mg/ml; H9.2), collagenase I (2 mg/ml) and/or trypsin/EDTA (0.25%/1 mmol/l; hES3, hES3-ENVY, hES2, iPS NJ, iPS I2) as described elsewhere (Kehat et al. J Clin Invest 108: 407-414 (2001); Mummery et al. Circulation 107: 2733-2740 (2003); Xu et al. Circ Res 91: 501-508 (2002); Yang et al. Nature 453: 524-528 (2008); Passier et al. Stem Cells 23: 772-780 (2005); each incorporated herein by reference). Cardiomyocytes were counted in representative aliquots of enzymatically dispersed cells after staining of tropomyosin or sarcomeric actinin.

Basic Human Engineered Heart Muscle (hEHM) Construction

The inventors constructed hEHMs using a modified EHM-engineering protocol (Zimmermann et al. Circ Res 90: 223-230 (2002), incorporated herein by reference). Briefly, EHMs (reconstitution volume: 450 μl) were prepared by pipetting a mixture containing freshly dispersed ESC-derivatives ($1\times10^4$-$15\times10^6$ cells in Iscove-Medium with 20% fetal calf serum, 1% non-essential amino acids, 2 mmol/l glutamine, 100 μmol/l β-mercaptoethanol, 100 U/ml penicillin, and 100 mg/ml streptomycin), pH-neutralized collagen type I from rat tails (0.4 mg/EHM), Matrigel™ (10% v/v; Becton Dickenson or tebu), and concentrated serum-containing culture medium (2× DMEM, 20% horse serum, 4% chick embryo extract, 200 U/ml penicillin, and 200 mg/ml streptomycin) in circular molds (inner/outer diameter: 2/4 mm; height: 5 mm) (Table 1). hEHM condensed quickly within the casting molds and were transferred onto static stretch devices (110% of slack length) (Zimmermann et al. Nat Med 12: 452-458 (2006), incorporated herein by reference) on culture day 3. Medium was changed every other day. hEHM culture under stretch was performed for 7 days.

Another detailed prior art protocol which is suitable to serve as a basis for the improved method disclosed herein is described by Soong et al. Curr Prot Cell Biol. 23.8.1-23.8.21 (2012), which is incorporated herewith in its entirety, and in particular reference is made to the "Basic Protocol 2", and the "Support Protocol 2".

Withdrawal and Replacement of Xenogenic Matrix Components

A protocol with reduced xenogenic components (Matrix protocol, Table 1) was established to enable pre-GMP hEHM. Cells were reconstituted in a mixture of pH-neutralized bovine collagen (Devros Medical, 0.4 mg/EHM), concentrated serum-containing culture medium (2× DMEM, 40% fetal calf serum, 200 U/ml penicillin, and 200 mg/ml streptomycin) and cultured in Iscove-Medium with 20% fetal calf serum, 1% non-essential amino acids, 2 mmol/l glutamine, 0.3 mmol/l ascorbic acid, 100 µmol/l β-mercaptoethanol, 100 U/ml penicillin, and 100 µg/ml streptomycin.

Withdrawal and Replacement of Xenogenic Medium Components

To generate fully defined, serum-free EHM cells were reconstituted in a mixture of pH-neutralized bovine collagen (Devros Medical, 0.4 mg/EHM), concentrated serum-free medium medium (2× DMEM, 8% B27, 200 U/ml penicillin, and 200 mg/ml streptomycin) and cultured in Iscove-Medium with full 4% B27, 1% non-essential amino acids, 2 mmol/l glutamine, 0.3 mmol/l ascorbic acid, 20 ng/ml IGF-1, 10 ng/ml FGF2, 10 ng/ml VEGF, 5 ng/ml TGFb1 (culture day 0-3 only), and 100 U/ml penicillin, and 100 µg/ml streptomycin (Serum-free protocol, Table 1). B27 supplement contains vitamins (Biotin, DL Alpha Tocopherol, Acetate DL Alpha-Tocopherol, Vitamin A), proteins and enzymes (BSA, fatty acid free Fraction V, Catalase, Human Recombinant Insulin, Human Transferrin, Superoxide Dismutase), and other cell-supporting components (Corticosterone, D-Galactose, Ethanolamine, Glutathione (reduced), L-Carnitine, Linoleic Acid, Linolenic Acid, Progesterone, Putrescine, Sodium Selenite, and T3 (triodo-I-thyronine). Where indicated full B27 (Invitrogen, A1486701) was compared to B27 without antioxidants (Invitrogen, #10889038) and B27 without insulin (Invitrogen, #0050129SA). B27 supplement was replaced by a custom-made supplement consisting of Albumin, Transferrin, Ethanolamine, Sodium selenite, L-Carnitine HCl, Hydrocortisone, Fatty acid supplement, and Triiodo-L-thyronine (Table 2).

Analyses of Contractile Function

The inventors analyzed force of contraction and twitch kinetics (contraction time: time from 50% to maximal contraction; relaxation time: time from maximal contraction to 50% relaxation) under isometric conditions as described before (Zimmermann et al. *Circ Res* 90: 223-230 (2002), incorporated herein by reference). Contraction frequency was assessed by light microcopy (unstimulated spontaneous contractions) immediately after removing EHMs from the incubator.

Flow Cytometry

EBs cultured in different medium conditions were made into a single cell suspension as described above. Cells were fixed in 70% ice cold ethanol under constant mixing. The cells were stained for sarcomeric actinin (Sigma) to label cardiomyocytes and DAPI to analyze nuclear DNA content and to exclude cell doublets. Cells were run on a LSRII Cytometer (BD). At least 10,000 live cells were analyzed. The following parameters were then analyzed, (1) cell death (percentage of cells in the sub-G1 fraction), (2) cardiomyocyte and non-myocyte percentage (Actinin-positive and negative cells, respectively) (3) Cardiomyocte maturation (mean actinin fluorescence), (4) cardiomyocyte and (5) non-myocyte size (based on sideward scatter area, SSC-A).

Morphological Analyses hEHMs were fixed in neutral buffered 4% formaldehyde/1% methanol, pH 7.4 for confocal laser scanning microscopy (CLSM; Zeiss 510 Meta LSM system or Zeiss 710 LSM) respectively as described earlier (Zimmermann et al. Circ Res 90: 223-230 (2002), incorporated herein by reference). For CLSM, the inventors prepared vibratome sections (100 µm; Leica VT1000 S) and subjected them to immune fluorescent labeling with antibodies directed against α-sarcomeric actinin (Sigma clone EA-53, 1:800; with appropriate secondary antibodies). Nuclei were stained with DAPI (4',6-diamidino-2-phenylindole; 1 µg/ml).

Statistical Analysis

Data are presented as mean±standard error of the mean. Statistical differences were determined using paired and unpaired two-tailed Student's t-tests or ANOVA followed by Dunnett's post hoctest as indicated. A Pvalue<0.05 was considered statistically significant.

Results

Generation of Human Engineered Heart Muscle (hEHM)

Figure 1:
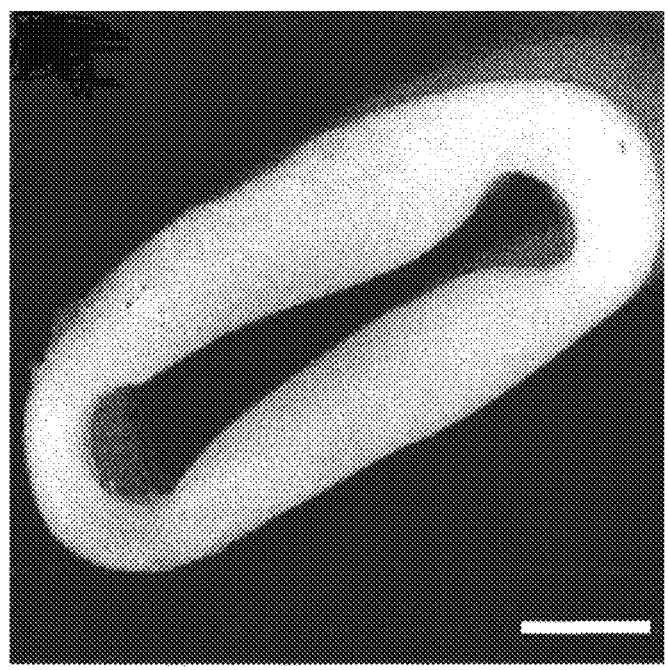
FIG. 1. hEHM formation. hEHM after 10 days in culture (3 days in the casting mold followed by 7 days on a custom made spacer; culture day 3+7). Bar: 1 mm (.

EBs—prepared in Haifa (H9.2;), Singapore (hES3 and hES3-ENVY; Costa et al. *Nat Methods* 2: 259-260 (2005)), and Toronto (hHES2; iPS)—were sent to Hamburg/Gottingen by express mail at room temperature in an air-tight container filled with culture medium. Delivery was ensured within 72-96 h. After arrival, EBs were transferred into fresh culture medium and allowed to recover for 24-48 h. Within that time EBs regained spontaneous contractile activity. EBs were enzymatically dispersed EBs and the resulting single cell suspensions allocated to hEHM generation or cytohistology. An initial series of experiments explored the number of necessary cell quantity per hEHM ($1\times10^4$-$15\times10^6$ cells) and utility of different ESC-lines (H9.2, hES2, hES3, hES3-ENVY) and iPS lines (I2, BJ, Sendai) for hEHM construction (n=67). Spontaneous beating of variably sized areas could be observed in all cultures within 48 h of hEHM casting. However, force-generating hEHMs formed only if $1.25\text{-}15\times10^6$ cells/EHM were utilized (FIG. 1). Depending on the size of the EHM, the cell density can easily be adapted.

Figure 2A:
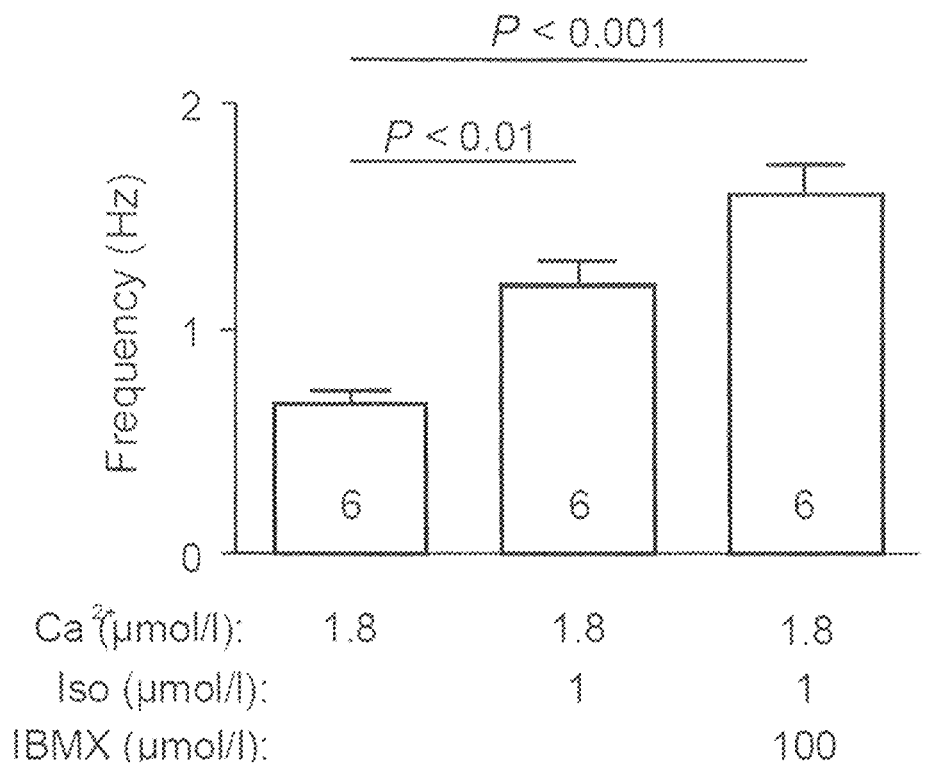
FIGS. 2A-2D. Characterization of hEHM contractile function. (A) Chronotropic response after stimulation with cAMP-elevating compounds (Iso: beta-adrenergic stimulation; IBMX: phosphodiesterase inhibition, n=6/group). (B) Inotropic response of hEHMs to increasing concentrations of extracellular calcium, comparison of hES2 (n=12), hES3 (n=12) and iPS 12 (n=3) (C) Inotropic response of hEHMs (hES2) to isoprenaline (triangles) and carbachol (squares) stimulation. Inset: normalized twitches at low calcium (lowest graph), stimulation with isoprenaline (highest graph) and carbachol (middle graph). (D) Relaxation of hEHMs with isoprenaline (triangles) and carbachol (squares) stimulation. Inset: normalized twitches *P<0.05 vs. baseline values (A: paired two-tailed Student's t-test; C, D: ANOVA followed by Dunnet's post hoc test).
Figure 2B:
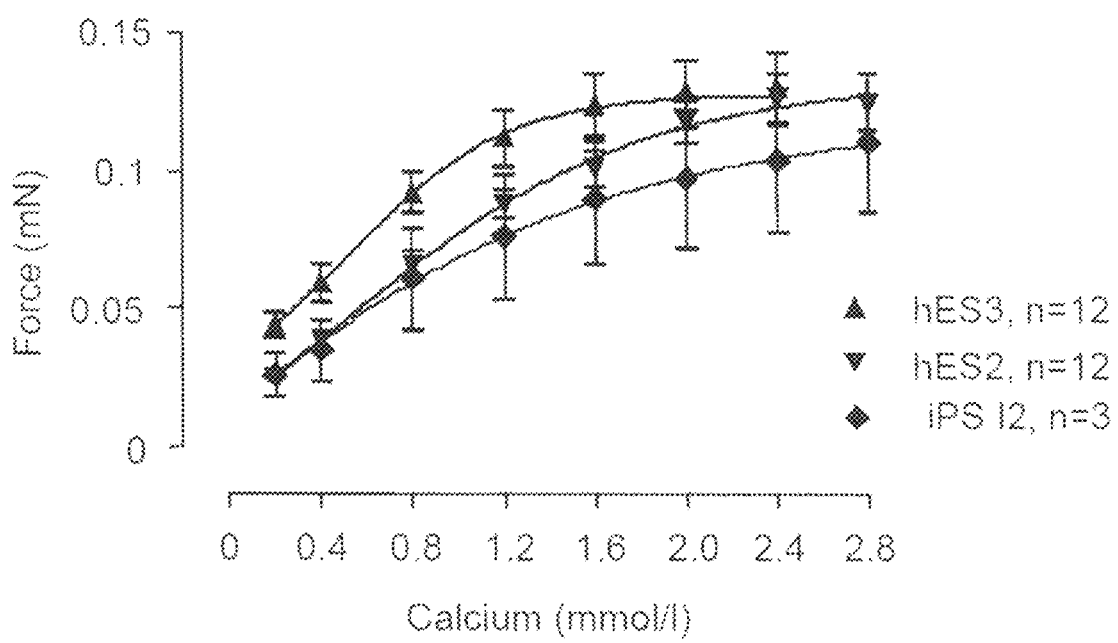
Figure 2C:
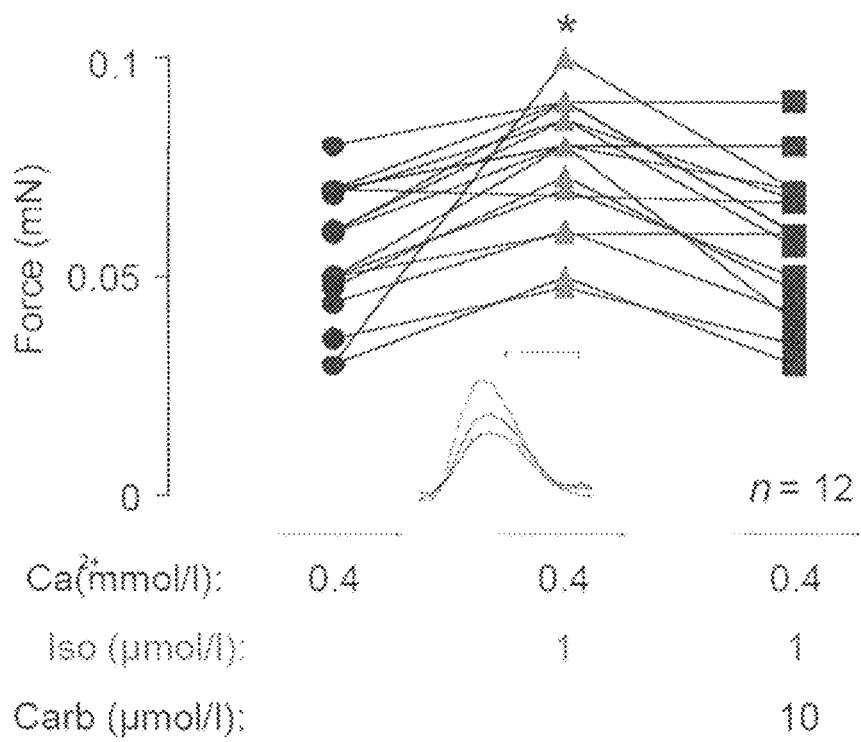
Figure 2D:
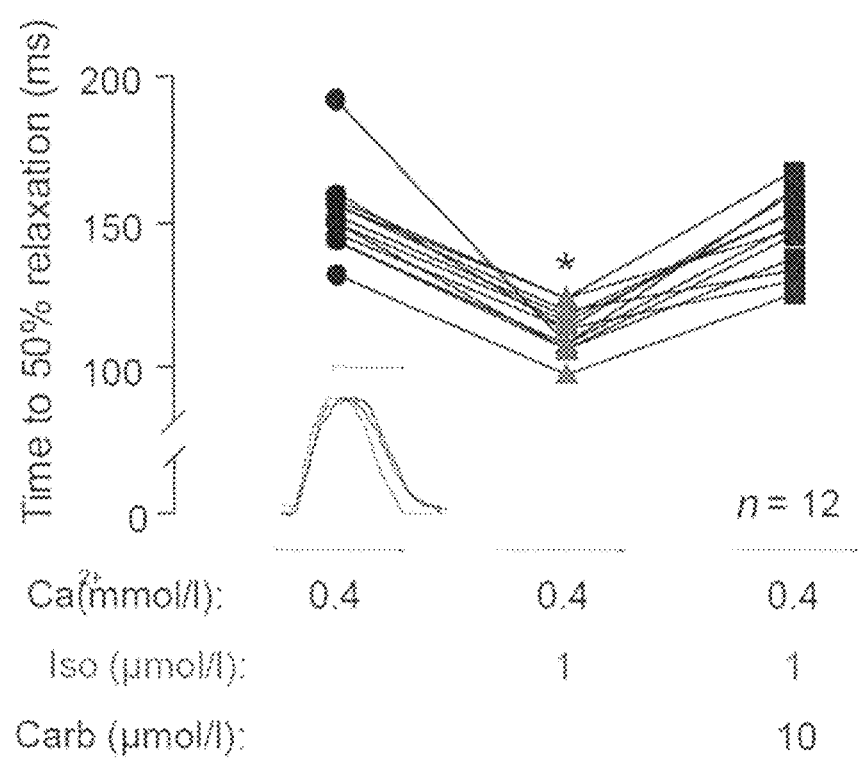

Organotypic Function of hEHM hEHMs contracted stably and rhythmically (0.8±0.05 Hz at 37° C.; n=14) for at least 3 weeks in culture. The inventors performed a detailed functional characterization at 10 days. Incubation with isoprenaline increased spontaneous beating frequency to 1.2±0.1 Hz (n=6; P<0.01 FIG. 2A). Additional inhibition of phosphodiesterase with 3-isobutyl-1-methylxanthine (IBMX; 100 µmol/l) caused a further increase in spontaneous beating rate to 1.6±0.1 Hz (n=6; P<0.001 FIG. 2A). hEHM developed maximal twitch mean forces of 130±13 µN at 2.4 mmol/l calcium ($EC_{50}$: 0.8±0.04 mmol/l, n=17; FIG. 2B). β-Adrenergic stimulation with 1 µmol/l isoprenaline at sub-$EC_{50}$ extracellular calcium (0.4 mmol/l) increased force of contraction by 47±12% (n=12; FIG. 2C) and shortened relaxation to 113±2.3 ms (n=12; FIG. 2D).

Importance of Non-Myocytes in EHM Formation

Figure 3A:
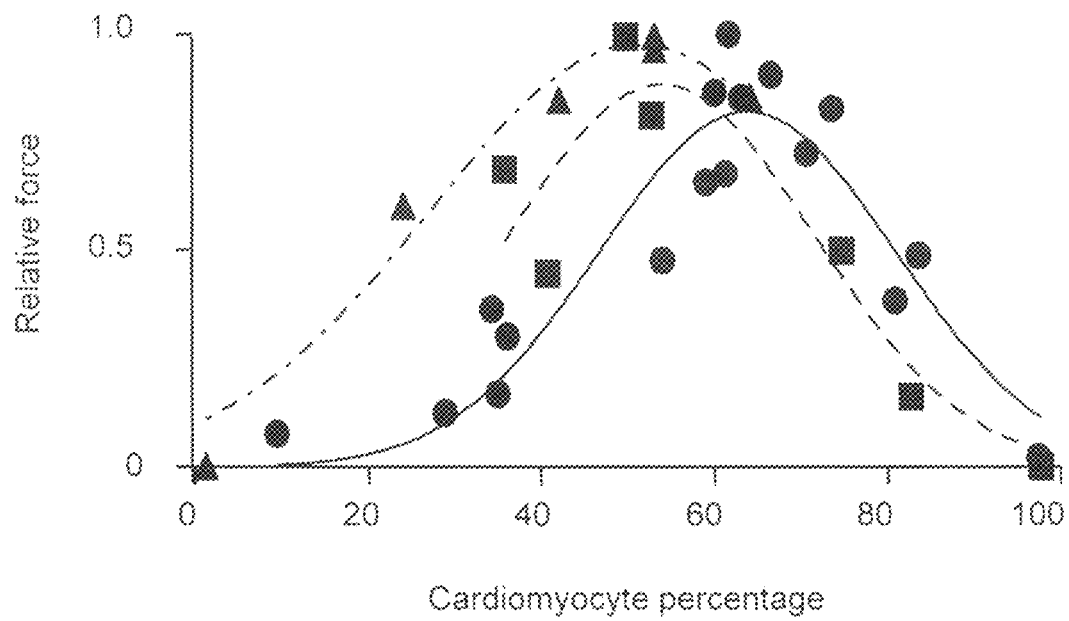
FIGS. 3A-3B. Importance of non-myocytes for EHM formation. (A) Normalized force compared to cardiomyocyte percentage (actinin+ cells) of EHM generated from hES2 line (circles: monolayer cardiac differentiation protocol (Hudson, et al. Stem Cells Dev 21: 1513-1523 (2012)), -squares: EB cardiac differentiation protocol (Yang et al. *Nature* 453: 524-528 (2008))) and iPS BJ line (triangles).

All ESC-lines and iPS lines utilized here appeared to be suited for hEHM generation. To test which cardiomyocyte content is optimal for a force generating tissue, the inventors plotted developed force against the cardiomyocyte percentage. Interestingly, a bell-shaped distribution with highest forces developed at a cardiomyocyte percentage of 40-80% was found (FIG. 3A).

Figure 3B:
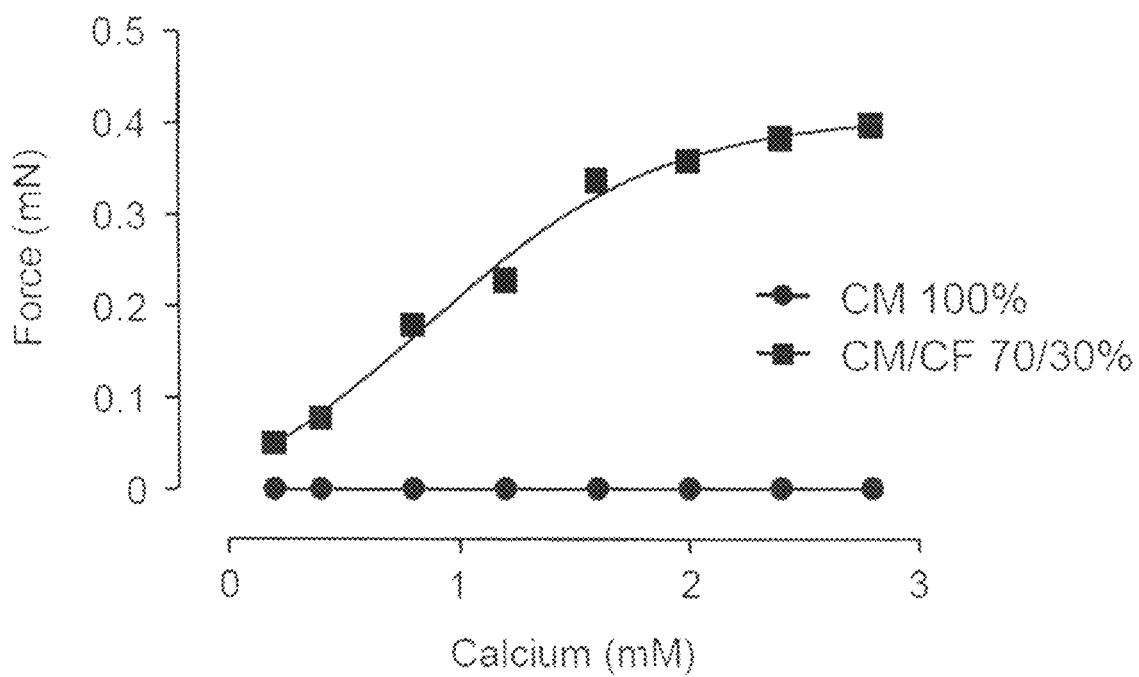

This observation suggests a critical role of non-myocytes for proper tissue formation. To investigate this the inventors performed experiment with human cardiomyocytes that were purified by the surface marker CD172a (SIRPa) (Dubois et al. *Nat Biotechnol* 29: 1011-1018 (2011)). EHMs generated from purified cardiomyocytes did not form force-generating tissue (FIG. 3B). Supplementation with 30% human cardiac fibroblasts, however, yielded a stiffer tissue with good force production. These results emphasize that non-myocytes are vital to cardiac tissue formation and that these cells also need to be supported under serum-free conditions.

Generation of hEHM with GMP-Compatible Matrix

The inventors initially constructed hEHMs based on a protocol that the inventors had developed in a neonatal rat heart cell model (Zimmermann et al. *Biotechnol Bioeng* 68: 106-114 (2000)). This protocol includes several non-human components (including rat collagen, Matrigel, horse serum, fetal calf serum, and chick embryo extract) that are incompatible with a "therapeutic application" in vivo. To address this caveat, a series of experiments directly testing whether non-human components of the hEHM-matrix could be reduced were first conducted. Rat collagen was replaced with medical grade (GMP) bovine collagen without loss of performance (FIG. 4A). Also, Matrigel®, horse serum and chick embryo extract could be left out without negative impact on hEHM formation and function ("Matrix protocol", FIG. 4B, Table 1). Complementing bovine collagen with other extracellular matrix proteins such as fibronectin and laminin, one of the major components of Matrigel®, did not yield additional benefit (FIG. 4C).

Definition of Serum-Free Medium to Support hEHM Formation

To further define the human EHM culture and make it GMP compatible, the inventors sought to replace all undefined serum component with chemically defined supplements. To screen for these supplements the inventors introduced a simplified screening algorithm based on 3D-human embryoid body (EB) cultures. ESCs for this screen were cultured under serum-free conditions (Yang et al. *Nature* 453: 524-528 (2008); Kattman et al. *Cell Stem Cell* 8: 228-240 (2011)). The reference for the screens was our serum-containing EHM medium (Table 1): (1) Iscove's, (2) 2 mmol/L L-glutamine, (3) 20% FBS, (4) 1% non-essential amino acids, (5) 0.3 mmol/L ascorbic acid, (6) 100 μmol/l β-mercaptoethanol, (7) 100 U/ml Penicillin/100 mg/ml Streptomycin. As read outs for the beneficial or detrimental role of basal culture medium and supplements a flow cytometry-based protocol (Tiburcy et al. *Circ Res* 109: 1105-1114 (2011); incorporated herein by reference) was established to determine (1) cell death (based on sub-G1 DNA content), (2) cardiomyocyte content (based on actinin expression), (3) cardiomyocyte maturation (based on actinin mean fluorescence per cardiomyocyte), (4) cardiomyocyte size, and (5) non-myocyte size (based on sideward scatter area).

The inventors first screened three basal media formulations (Iscove's, RPMI, αMEM: Table 3-5) with and without B27 supplementation. B27 has been used by several groups for differentiation of human ESCs and iPSCs (Burridge et al. *Cell Stem Cell* 10: 16-28 (2012)). The screen demonstrated that B27 was essential for EB formation irrespective of the tested basal medium. Iscove's and RPMI showed comparable results while αMEM appeared to cause slightly higher cell death. On the other hand, αMEM was superior for cardiomyocyte actinin expression (FIG. 5A).

Given own preliminary findings showing suboptimal performance of EHMs cultured in the presence of basal RPMI (FIGS. 7A-7D), the inventors continued the screen with Iscove's or αMEM as basal medium. The inventors next scrutinized the utility of B27 in its standard formulation with and without insulin. 4% B27 supplementation with insulin (10 μg/ml final concentration) showed lowest cell death and possibly greater non-myocyte support (lower cardiomyocytes percentage suggest a shift to more non-myocytes) as compared to B27 without insulin and lower B27 (2%) supplement concentration (FIG. 5B). The inventors next screened the utility of 6 peptide growth factors at above EC50 concentrations and fatty acid supplements. PDGF-BB, CT-1 and Neuregulin-1 caused substantial cell death whereas IGF-1 appeared to protect from cell death (FIG. 6A,B). TGFβ1, VEGF and fatty acid supplements enhanced individual cardiomyocyte actinin expression. FGF-2 supported non-myocyte growth and increased cardiomyocyte cell size (FIG. 6A). TGFβ2 had no beneficial effect (FIG. 6B). All of the tested compounds or combinations thereof were implicated in cardiac development and EHM generation (Naito et al. *Circulation* 114: 172-78 (2006); Shimojo et al. *Am J Physiol Heart Circ Physiol* 293: H474-481 (2007); Vantler et al. *J Mol Cell Cardiol* 48: 1316-1323 (2010); Odiete et al. *Circ Res* 111: 1376-1385 (2012); Wollert & Chien *J Mol Med* (Berl) 75: 492-501 (1997); Price et al. *Anat RecA Discov Mol Cell Evol Biol* 272: 424-433 (2003); Molin et al. *Dev Dyn* 227: 431-444 (2003); Corda et al. *Circ Res* 81: 679-687 (1997); Lopaschuk & Jaswal *J Cardiovasc Pharmacol* 56: 130-140; all incorporated herein by reference).

EHM development is characterized by two stages. Initially there is a "condensation phase" where the isolated cells are "settling in" the matrix, reorganizing themselves and the matrix which may also be accompanied by substantial cell death. This stage is greatly influenced by the non-myocytes. The second stage is the maturation of the tissue under mechanical load. This phase is characterized by hypertrophic growth and maturation of cardiomyocytes, alignment, increasing force development, and matrix stabilization (Tiburcy et al. *Circ Res* 109: 1105-1114 (2011)).

Figure 7A:
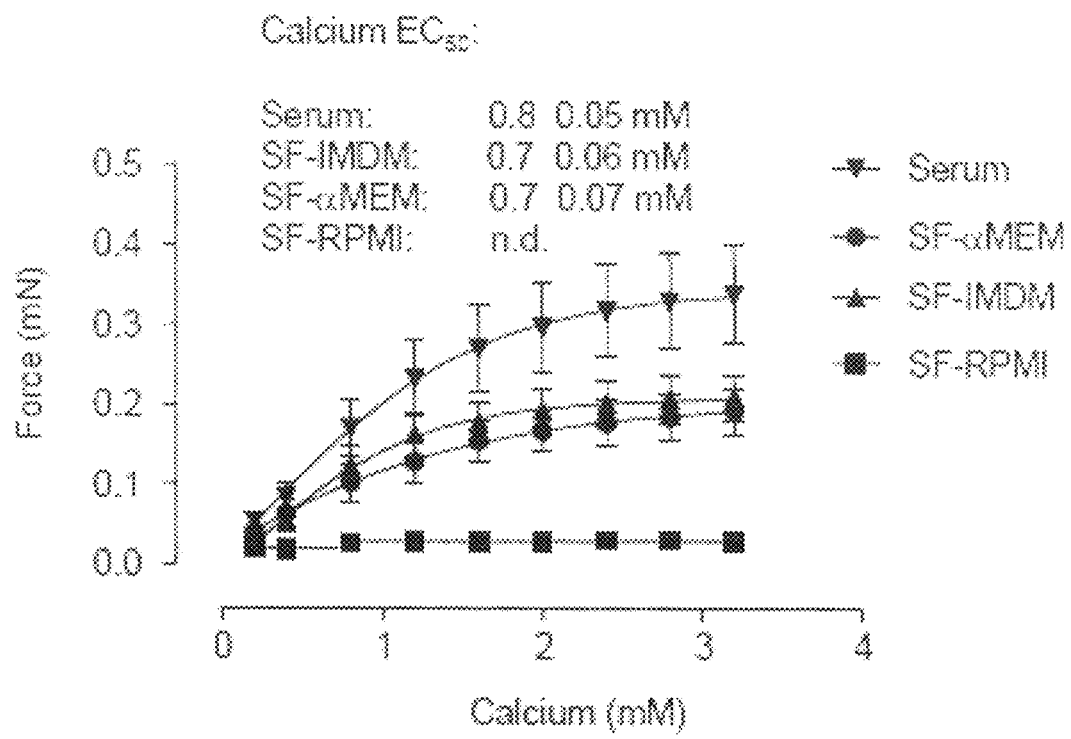
Figure 7B:
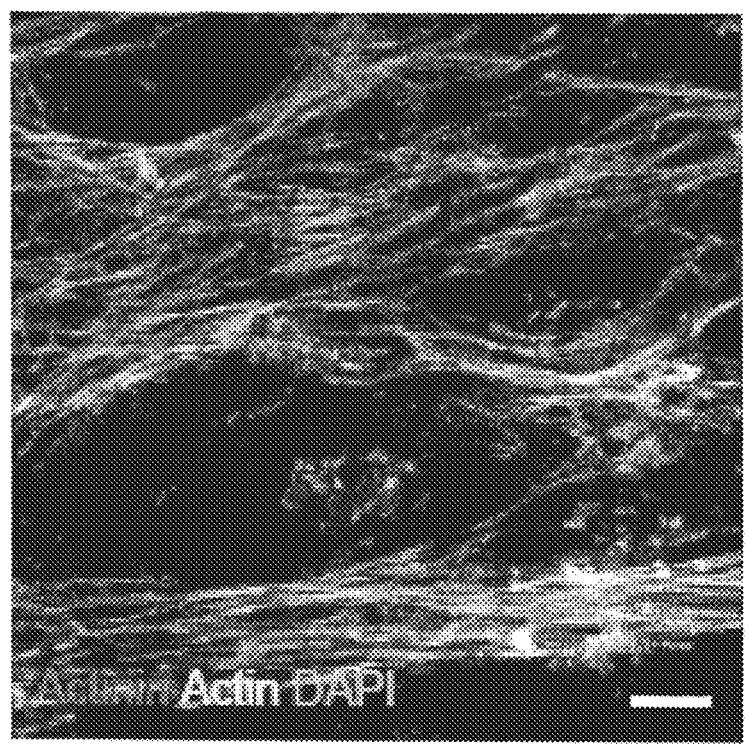
Figure 7C:
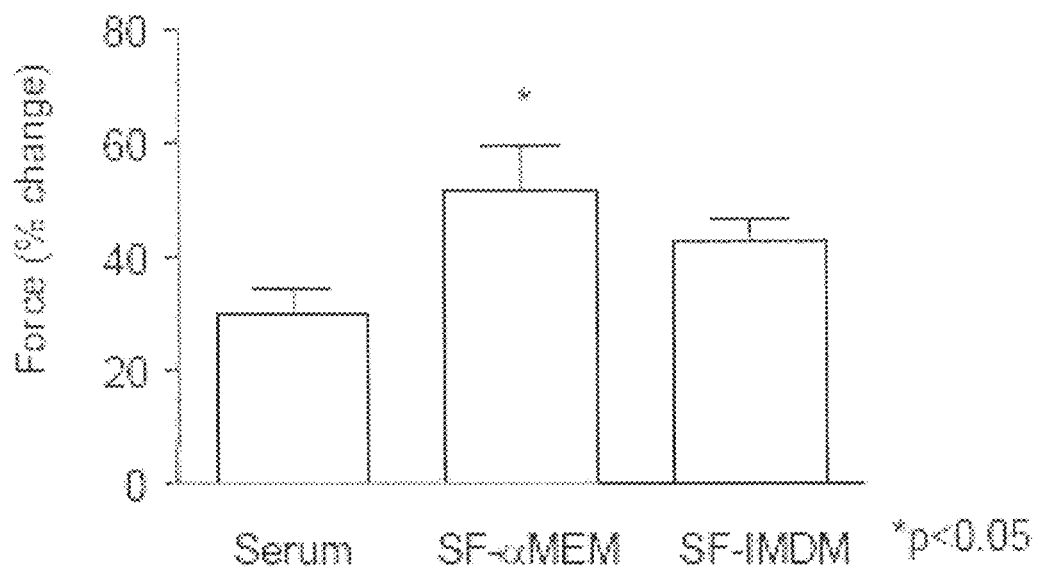
Figure 7D:
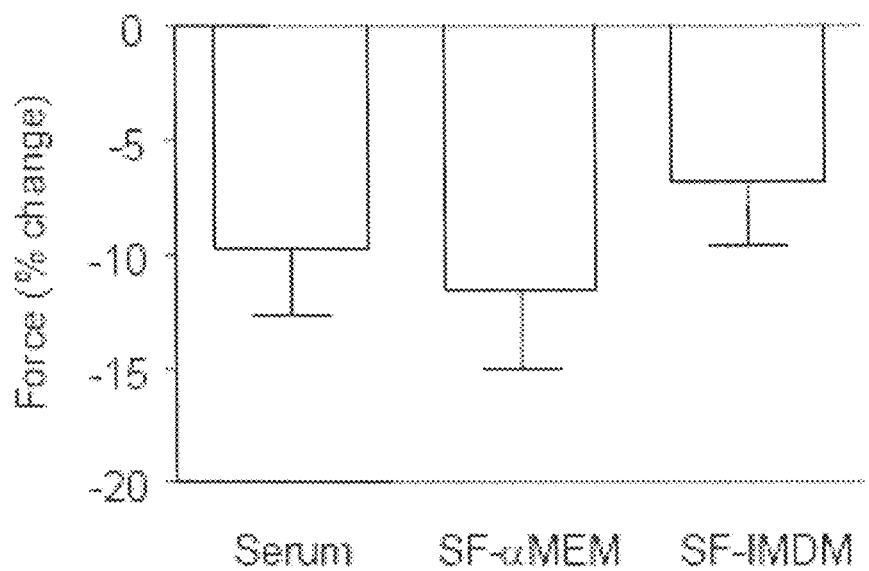

The inventors reasoned that according to the stage different medium conditions may be required. To prevent cell death during the condensation phase the inventors chose a combination of medium components that were neutral or even reducing cell death in the initial screen. This is Iscove's basal medium, 4% B27, and IGF-1. Also, the matrix reorganisation and condensation through non-myocytes was supported by factors that increase number and/or size of non-myocytes (IGF-1, TGF-beta1, FGF-2, in the first stage). VEGF is added for support of cardiomyocyte maturation (Table 5). This medium was then tested for its ability to support the formation of force-generating EHM. Serum-free EHM were beating coherently at a spontaneous beating frequency of 113±12 bpm, n=7. Serum containing EHM were beating significantly faster (199±8 bpm, n=8). The inventors found a similar maximal force development and calcium sensitivity compared to the serum containing control (FIG. 7A). Both, Iscove's and αMEM basal medium supported EHM formation with comparable results in contractile force. RPMI did not support force-generating tissue (FIG. 7A, Table 5, 6). Morphologically, serum-free EHM contained well developed muscle bundles with anisotropically aligned cardiomyocytes (FIG. 7B). Importantly, the serum-free EHM responded to adrenergic and muscarinic stimulation as expected for heart muscle. In fact the αMEM EHM responded significantly better than serum-containing controls. (FIG. 7 C, D).

Figure 8A:
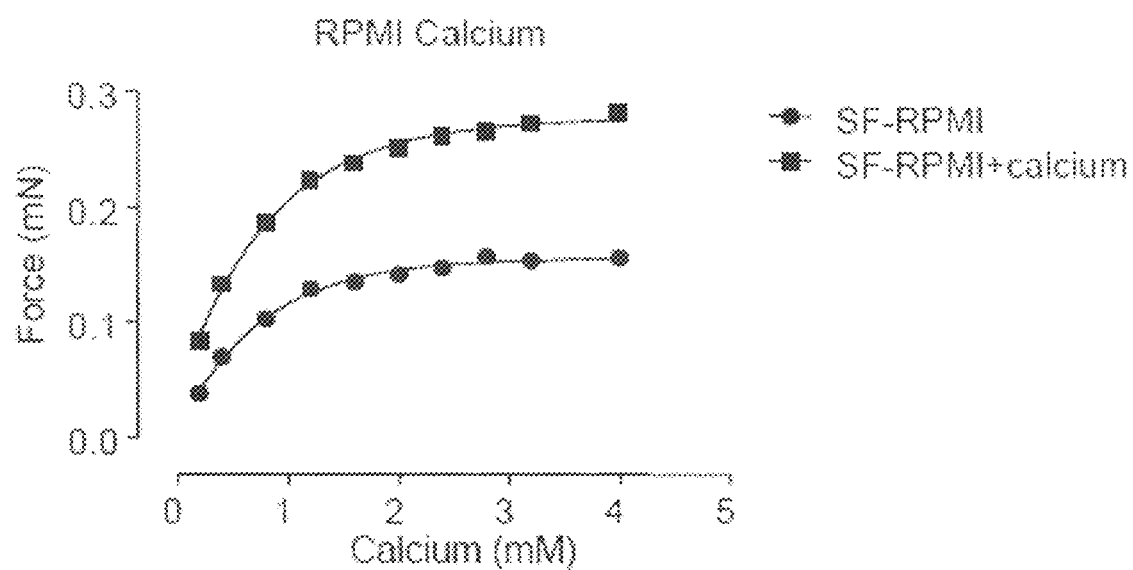
Figure 8B:
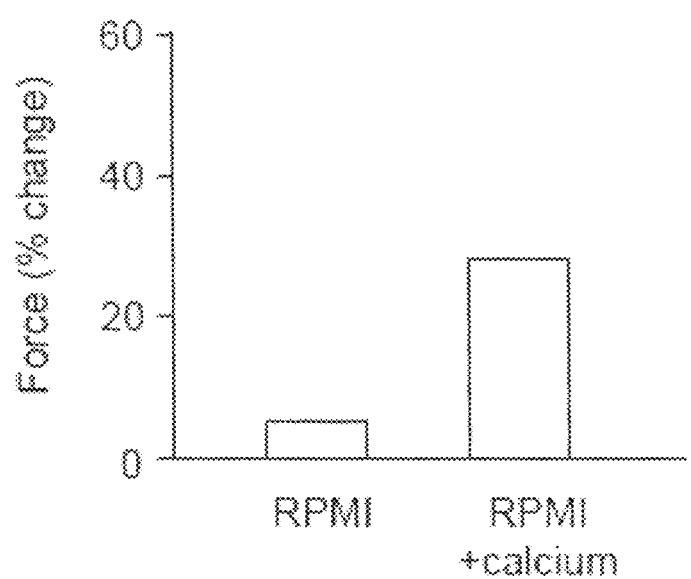

The inventors hypothesized that the insufficient performance of RPMI medium was due to the lower than physiological free calcium concentration of RPMI medium (0.424 mmol/L, Table 4). To test if this was true the inventors performed an additional experiment to compare RPMI medium with RPMI medium with 0.8 mM CaCl added (final free calcium concentration 1.242 mmol/L). While EHM with RPMI hardly contracted supplementation of calcium lead to measurable maximal force and better responsiveness to isoprenalin (FIGS. 8A-8B). In fact maximal force production with supplemented RPMI was comparable to IMDM or αMEM medium (FIG. 7A) suggesting that a range of ~1-2 mmol/L calcium is required for proper tissue function.

To verify the results from the initial screen, the inventors additionally tested the influence of critical factors on the formation of functional EHM. TGFβ1 addition from day 0 to 3 was essential, but prolonged TGFβ1 treatment did not yield an additional benefit (FIG. 9A, B). Both FGF and VEGF were able to enhance force-generation confirming an important contribution to tissue formation (FIG. 10).

Increasing the B27 supplement concentration to 4% was superior to 2% B27 (FIG. 11). To test which components of B27 are essential for EHM function the inventors first performed an experiment with different commercially available B27 formulations. the inventors compared full B27 with B27 minus insulin, and B27 minus antioxidants. B27 minus antioxidants performed comparable to full B27 suggesting that antioxidants are not required. Surprisingly, B27 minus insulin performed better than full B27 implying that insulin supplementation is also not required (FIG. 12).

Based on these results the inventors then developed a custom-made serum supplement to replace B27 (Table 7). When the inventors tested this custom-made serum supplement against serum-containing medium and serum-free medium with B27 minus insulin the inventors found comparable maximal force development suggesting that B27 can be omitted from the serum-free EHM culture and replaced by custom-made serum supplement (FIG. 13A). These findings were confirmed with hEHM from iPSC demonstrating utility for generation of defined engineered heart muscle from different pluripotent stem cell sources. (FIG. 13B).

To investigate if serum-free hEHM supports long-term culture and maturation of cardiomyocytes the inventors tested force production of serum-free hEHM from hIPS-G1 at week 2, week 4, and week 8 of culture. The inventors observed a strong increase in force production (FIG. 14A) and rod-shaped morphology with regular cross striation of individual hEHM-derived cardiomyocytes (FIG. 14B) indicating well advanced maturation under serum-free conditions.

CONCLUSION

This study demonstrates for the first time that differentiated, force-generating human heart muscle can be generated in vitro under fully defined, serum-free conditions. The protocol works for embryonic (ESC) and induced pluripotent (iPS) stem cells-derived heart muscle.

This is a major breakthrough which enables future in vitro studies to investigate e.g. maturation and hypertrophy without confounding serum factors but also potential in vivo applications and therapeutic approaches under GMP regulations.

LIST OF REFERENCES

WO 01/55297
WO 2007/054286
WO 2008/058917
Zimmermann, Kardiale Regeneration mit künstlichem Herzgewebe. Universitätsklinikum Hamburg Eppendorf, Habilitation (2006)
Schneiderbanger, Zur Bedeutung von Tranforming Growth Factor-β1 und Interleukin-1β für die Morphologie, die Genexpression und die kontraktile Funktion von rekonstituiertem dreidimensionalen künstlichen Herzmuskelgewebe. Universität Hamburg, Dissertation (2006)
Eschenhagen, T. & Zimmermann, W. H. Engineering myocardial tissue. Circ Res 97, 1220-1231 (2005).
Zimmermann, W. H., et al. Heart muscle engineering: an update on cardiac muscle replacement therapy. Cardiovasc Res 71, 419-429 (2006).
Eschenhagen, T., et al. Three-dimensional reconstitution of embryonic cardiomyocytes in a collagen matrix: a new heart muscle model system. Faseb J 11, 683-694 (1997).
Kofidis, T., et al. In vitro engineering of heart muscle: artificial myocardial tissue. J Thorac Cardiovasc Surg 124, 63-69 (2002).
Moffitt, A. N., et al. Cardiac tissue engineering in an in vivo vascularized chamber. Circulation 115, 353-360 (2007).
Radisic, M., et al. Functional assembly of engineered myocardium by electrical stimulation of cardiac myocytes cultured on scaffolds. Proc Natl Acad Sci USA 101, 18129-18134 (2004).
Shimizu, T., et al. Fabrication of pulsatile cardiac tissue grafts using a novel 3-dimensional cell sheet manipulation technique and temperature-responsive cell culture surfaces. Circ Res 90, e40 (2002).
Zimmermann, W. H., et al. Three-dimensional engineered heart tissue from neonatal rat cardiac myocytes. Biotechnol Bioeng 68, 106-114 (2000).
Tulloch, N. L., et al. Growth of engineered human myocardium with mechanical loading and vascular coculture. Circ Res 109, 47-59 (2011).
Tiburcy, M., et al. Terminal differentiation, advanced organotypic maturation, and modeling of hypertrophic growth in engineered heart tissue. Circ Res 109, 1105-1114 (2011).
Zimmermann, W. H., et al. Tissue engineering of a differentiated cardiac muscle construct. Circ Res 90, 223-230 (2002).
Zimmermann, W. H., et al. Engineered heart tissue grafts improve systolic and diastolic function in infarcted rat hearts. Nat Med 12, 452-458 (2006).
Schaaf, S., et al. Human engineered heart tissue as a versatile tool in basic research and preclinical toxicology. PLoS One 6, e26397 (2011).
Naito, H., et al. Optimizing engineered heart tissue for therapeutic applications as surrogate heart muscle. Circulation 114, 172-78 (2006).
Thomson, J. A., et al. Embryonic stem cell lines derived from human blastocysts. Science 282, 1145-1147 (1998).
Takahashi, K. & Yamanaka, S. Induction of pluripotent stem cells from mouse embryonic and adult fibroblast cultures by defined factors. Cell 126, 663-676 (2006).
Schroeder, M., et al. Differentiation and lineage selection of mouse embryonic stem cells in a stirred bench scale bioreactor with automated process control. Biotechnol Bioeng 92, 920-933 (2005).
Kehat, I., et al. Human embryonic stem cells can differentiate into myocytes with structural and functional properties of cardiomyocytes. J Clin Invest 108, 407-414 (2001).
Mummery, C., et al. Differentiation of human embryonic stem cells to cardiomyocytes: role of coculture with visceral endoderm-like cells. Circulation 107, 2733-2740 (2003).
Xu, C., Police, S., Rao, N. & Carpenter, M. K. Characterization and enrichment of cardiomyocytes derived from human embryonic stem cells. Circ Res 91, 501-508 (2002).
Burridge, P. W., Keller, G., Gold, J. D. & Wu, J. C. Production of de novo cardiomyocytes: human pluripotent stem cell differentiation and direct reprogramming. Cell Stem Cell 10, 16-28 (2012).

Lian, X., et al. Robust cardiomyocyte differentiation from human pluripotent stem cells via temporal modulation of canonical Wnt signaling. Proc Natl Acad Sci USA (2012).

Costa, M., et al. The hESC line Envy expresses high levels of GFP in all differentiated progeny. Nat Methods 2, 259-260 (2005).

Yang, L., et al. Human cardiovascular progenitor cells develop from a KDR+ embryonic-stem-cell-derived population. Nature 453, 524-528 (2008).

Streckfuss-Bomeke, K., et al. Comparative study of human-induced pluripotent stem cells derived from bone marrow cells, hair keratinocytes, and skin fibroblasts. Eur Heart J, doi: 10.1093/eurheartj/ehs203 (2012).

Passier, R., et al. Increased cardiomyocyte differentiation from human embryonic stem cells in serum-free cultures. Stem Cells 23, 772-780 (2005).

Dubois, N. C., et al. SIRPA is a specific cell-surface marker for isolating cardiomyocytes derived from human pluripotent stem cells. Nat Biotechnol 29, 1011-1018 (2011).

Kattman, S. J., et al. Stage-specific optimization of activin/nodal and BMP signaling promotes cardiac differentiation of mouse and human pluripotent stem cell lines. Cell Stem Cell 8, 228-240.

Shimojo, N., et al. Contributory role of VEGF overexpression in endothelin-1-induced cardiomyocyte hypertrophy. Am J Physiol Heart Circ Physiol 293, H474-481 (2007).

Vantler, M., et al. PDGF-BB protects cardiomyocytes from apoptosis and improves contractile function of engineered heart tissue. J Mol Cell Cardiol 48, 1316-1323 (2010).

Odiete, O., Hill, M. F. & Sawyer, D. B. Neuregulin in cardiovascular development and disease. Circ Res 111, 1376-1385 (2012).

Wollert, K. C. & Chien, K. R. Cardiotrophin-1 and the role of gp130-dependent signaling pathways in cardiac growth and development. J Mol Med (Berl) 75, 492-501 (1997).

Price, R. L., et al. Effects of platelet-derived growth factor-AA and -BB on embryonic cardiac development. Anat Rec A Discov Mol Cell Evol Biol 272, 424-433 (2003).

Molin, D. G., et al. Expression patterns of Tgfbeta1-3 associate with myocardialisation of the outflow tract and the development of the epicardium and the fibrous heart skeleton. Dev Dyn 227, 431-444 (2003).

Corda, S., et al. Trophic effect of human pericardial fluid on adult cardiac myocytes. Differential role of fibroblast growth factor-2 and factors related to ventricular hypertrophy. Circ Res 81, 679-687 (1997).

Lopaschuk, G. D. & Jaswal, J. S. Energy metabolic phenotype of the cardiomyocyte during development, differentiation, and postnatal maturation. J Cardiovasc Pharmacol 56, 130-140.

Didié et al. Parthenogenetic stem cells for tissue-engineered heart repair. J Clin Invest. doi:10.1172/JCI66854.

Soong et al. Cardiac Differentiation of Human Enbryonic Stem Cells and their Assembly into Engineered Heart Muscle. Curr Prot Cell Biol. 55: 23.8.1-23.8.21, (2012).

Hudson, J., Titmarsh, D., Hidalgo, A., Wolvetang, E. & Cooper-White, J. Primitive cardiac cells from human embryonic stem cells. Stem Cells Dev 21, 1513-1523 (2012).

What is claimed is:

1. A method for producing engineered heart muscle (EHM), the method comprising the steps of:
   (i) providing a serum-free reconstitution mixture in one or more moulds, said reconstitution mixture comprising (a) a serum-free minimum essential medium; (b) a serum-free supplement resulting in a final concentration of 0.5-50 mg/ml albumin, 1-100 μg/ml transferrin, 0.1-10 μg/ml ethanol amine, 0.003-0.3 μg/ml sodium selenite, 0.4-40 μg/ml L-Carnitine HCl, 0.1-10 μg/ml Hydrocortisone, 0.05-5 μl/ml Fatty acid supplement, 0.0001-0.1 μg/ml triodo-L-thyronine (T3) and 0.2-2 mg/ml collagen; and (c) a mixture of human cardiac myocytes and human non-myocytes, wherein 20 to 80% of the total cell mixture are cardiac myocytes; wherein the reconstitution mixture has a pH of 7.2 to 7.6;
   (ii) culturing the serum-free reconstitution mixture in said one or more moulds, whereby the serum-free reconstitution mixture is allowed to condense for at least 15 min;
   (iii) culturing the mixture obtained in step (ii) in said one or more moulds in a serum-free EHM culture medium until the mixture condenses to at least 50% of its original thickness, wherein said EHM culture medium comprises (a) a basal medium comprising 0.5-3 mmol/L $Ca^{2+}$; (b) a serum-free supplement as defined in (i)(b); (c) 0.5-10 mmol/L L-glutamine; (d) 0.01-1.0 mmol/L ascorbic acid; (e) 1-100 ng/ml IGF-1; and (f) 1-10 ng/ml TGFβ1; and
   (iv) culturing the mixture obtained in step (iii) under mechanical stretching in a serum-free EHM culture medium as defined in step (iii) (a)-(f), whereby force-generating EHM is formed.

2. The method of claim 1, wherein the minimum essential medium in step (i) is selected from Iscove's medium, αMEM, DMEM, and RPMI.

3. The method of claim 1, wherein the serum-free supplement of step (i), step (iii), or both step (i) and step (iii) further comprises one or more components selected from the group consisting of vitamin A, D-galactose, linoleic acid, linolenic acid, progesterone, and putrescine.

4. The method of claim 1, wherein the serum-free supplement in component (b) of step (i), in component (b) of step (iii), or in component (b) of both step (i) and step (iii) is B27® supplement or B27® supplement minus insulin.

5. The method of claim 1, wherein said reconstitution mixture of step (i) comprises 0.3-0.5 mg collagen per $1.5 \times 10^6$ cardiac myocytes and non-myocyte cells.

6. The method of claim 1, wherein said collagen of the reconstitution mixture of step (i) is of medical grade and selected from the group consisting of collagen type I, collagen type III, collagen type V, and a mixture thereof.

7. The method of claim 6, wherein at least 90% of said collagen of the reconstitution mixture of step (i) is collagen type I, and wherein said collagen of the reconstitution mixture of step (i) further comprises one or more extracellular matrix components selected from the group consisting of elastin, laminin, entactin, nidogen, proteoglycan, and fibronectin.

8. The method of claim 1, wherein the reconstitution mixture of step (i) has a pH of 7.3 to 7.5.

9. The method of claim 1, wherein the cardiac myocytes are provided in admixture with cells of one or more class of cells selected from the group of non-myocytes consisting of fibroblasts, endothelial cells, smooth muscle cells, and mesenchymal stem cells, wherein the cardiac myocytes admixture contains 20-80% cardiac myocytes.

10. The method of claim 1, wherein the cardiac myocytes are provided in step (i) in a cell concentration of at least $2.7\text{-}20 \times 10^6$ per ml.

11. The method of claim 1, wherein culturing in step (ii) is carried out for 0.25-3 h.

12. The method of claim 1, wherein the serum-free EHM culture medium further comprises about 20 ng/ml human IGF1.

13. The method of claim 1, wherein the serum-free EHM culture medium further comprises about 5 ng/ml human TGFβ1.

14. The method of claim 1, wherein the serum-free EHM culture medium further comprises about 5-20 ng/ml human VEGF.

15. The method of claim 1, wherein the serum-free EHM culture medium further comprises about 5-20 ng/ml human FGF.

16. The method of claim 1, wherein the serum-free EHM culture medium in step (iii) additionally comprises 750 mg/L glycine, 890 mg/L L-alanine, 1320 mg/L L-asparagine, 1330 mg/L L-aspartic acid, 1470 mg/L L-glutamic acid, 1150 mg/L L-proline, and 1050 mg/L L-serine.

17. The method of claim 1, wherein culturing in step (iii) is carried out for at least 3 days.

18. The method of claim 1, wherein the culturing in step (iv) is carried out for a period of at least 3-60 days, wherein step (iv) is carried out on a stretch device.

19. The method of claim 18, wherein the stretch device applies a static, phasic or dynamic stretch.

* * * * *